United States Patent
Cohen

(10) Patent No.: US 7,686,770 B2
(45) Date of Patent: Mar. 30, 2010

(54) DISCRETE OR CONTINUOUS TISSUE CAPTURE DEVICE AND METHOD FOR MAKING

(75) Inventor: Adam L. Cohen, Van Nuys, CA (US)

(73) Assignee: Microfabrica Inc., Van Nuys, CA (US)

(*) Notice: Subject to any disclaimer, the term of this patent is extended or adjusted under 35 U.S.C. 154(b) by 608 days.

(21) Appl. No.: 11/582,049

(22) Filed: Oct. 16, 2006

(65) Prior Publication Data

US 2007/0100361 A1 May 3, 2007

Related U.S. Application Data

(60) Provisional application No. 60/726,794, filed on Oct. 14, 2005.

(51) Int. Cl.
*A61B 10/00* (2006.01)
*A61B 17/32* (2006.01)
*A61B 17/14* (2006.01)

(52) U.S. Cl. .................. 600/568; 600/562; 600/564; 600/570; 606/167; 606/176; 606/180

(58) Field of Classification Search .......... 600/562, 600/564, 568, 570; 606/167, 176, 180
See application file for complete search history.

(56) References Cited

U.S. PATENT DOCUMENTS

| | | | | |
|---|---|---|---|---|
| 5,190,637 A | | 3/1993 | Guckel | 205/118 |
| 5,562,102 A | * | 10/1996 | Taylor | 600/564 |
| 5,573,008 A | * | 11/1996 | Robinson et al. | 600/567 |
| 5,595,185 A | * | 1/1997 | Erlich | 600/567 |
| 5,971,939 A | * | 10/1999 | DeSantis et al. | 600/562 |
| 6,027,630 A | | 2/2000 | Cohen | 205/135 |
| 6,835,180 B2 | * | 12/2004 | Rudnick et al. | 600/562 |
| 7,445,603 B2 | * | 11/2008 | Zimmon | 600/564 |
| 2003/0033896 A1 | * | 2/2003 | Borowczak et al. | 73/866 |
| 2006/0236786 A1 | * | 10/2006 | Burton | 73/863 |

OTHER PUBLICATIONS

Cohen, et al., "EFAB: Batch Production of Functional, Fully-Dense Metal Parts with Micron-Scale Features", Proc. 9th Solid Freeform Fabrication, The University of Texas at Austin, Aug. 1998, pp. 161.
Adam L. Cohen, et al., "EFAB: Rapid, Low-Cost Desktop Micromachining of High Aspect Ratio True 3-D MEMS", Proc. 12th IEEE Micro Electro Mechanical Systems Workshop, IEEE, Jan. 17-21, 1999, pp. 244-251.

(Continued)

*Primary Examiner*—Max Hindenburg
*Assistant Examiner*—Sean P Dougherty
(74) *Attorney, Agent, or Firm*—Dennis R. Smalley

(57) ABSTRACT

Some embodiments of the invention provide an instrument for mechanically removing segments of tissue from a patient during a minimally invasive surgical procedure. An exemplary instrument provides an inlet for receiving tissue a mechanism for cutting away received tissue and for simultaneously moving the cut away tissue away from the inlet to allow additional material to enter the inlet for removal wherein multiple specimens can be captured and eventually removed from the patient's body without the need of removing the instrument after each capture.

17 Claims, 25 Drawing Sheets

OTHER PUBLICATIONS

"Microfabrication—Rapid Prototyping's Killer Application", Rapid Prototyping Report, CAD/CAM Publishing, Inc., Jun. 1999, pp. 1-5.

Adam L. Cohen, "3-D Micromachining by Electrochemical Fabrication", Micromachine Devices, Mar. 1999, pp. 6-7.

Gang Zhang, et al., "EFAB: Rapid Desktop Manufacturing of True 3-D Microstructures", Proc. 2nd International Conference on Integrated MicroNanotechnology for Space Applications, The Aerospace Co., Apr. 1999.

F. Tseng, et al., "EFAB: High Aspect Ratio, Arbitrary 3-D Metal Microstructures Using a Low-Cost Automated Batch Process", 3rd International Workshop on High Aspect Ratio Microstructure Technology (HARMST'99), Jun. 1999.

Adam L. Cohen, et al., "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, Sep. 1999.

F. Tseng, et al., "EFAB: High Aspect Ratio, Arbitrary 3-D Metal Microstructures Using a Low-Cost Automated Batch Process", MEMS Symposium, ASME 1999 International Mechanical Engineering Congress and Exposition, Nov. 1999.

Adam L. Cohen, "Electrochemical Fabrication (EFABTM)", Chapter 19 of the MEMS Handbook, edited by Mohamed Gad-El-Hak, CRC Press, 2002, pp. 19/1-19/23.

* cited by examiner

DISCRETE OR CONTINUOUS TISSUE CAPTURE DEVICE AND METHOD FOR MAKING

RELATED APPLICATIONS

This application claims the benefit of U.S. Provisional Patent Application No. 60/726,794, filed Oct. 14, 2005. This referenced application is in incorporated herein by reference as if set fourth in full.

FIELD OF THE INVENTION

The present invention relates generally to the field of micro-scale or meso-scale medical devices and particularly to micro-scale or meso-scale surgical tools and methods for making such devices or tools and in particular electrochemical fabrication methods where the devices or tools are formed from multiple layers of deposited and adhered materials.

BACKGROUND OF THE INVENTION

A technique for forming three-dimensional structures (e.g. parts, components, devices, and the like) from a plurality of adhered layers was invented by Adam L. Cohen and is known as Electrochemical Fabrication. It is being commercially pursued by Microfabrica Inc. (formerly MEMGen® Corporation) of Burbank, Calif. under the name EFAB™. This technique was described in U.S. Pat. No. 6,027,630, issued on Feb. 22, 2000. This electrochemical deposition technique allows the selective deposition of a material using a unique masking technique that involves the use of a mask that includes patterned conformable material on a support structure that is independent of the substrate onto which plating will occur. When desiring to perform an electrodeposition using the mask, the conformable portion of the mask is brought into contact with a substrate while in the presence of a plating solution such that the contact of the conformable portion of the mask to the substrate inhibits deposition at selected locations. For convenience, these masks might be generically called conformable contact masks; the masking technique may be generically called a conformable contact mask plating process. More specifically, in the terminology of Microfabrica Inc. (formerly MEMGen® Corporation) of Burbank, Calif. such masks have come to be known as INSTANT MASKS™ and the process known as INSTANT MASKING™ or INSTANT MASK™ plating. Selective depositions using conformable contact mask plating may be used to form single layers of material or may be used to form multi-layer structures. The teachings of the '630 patent are hereby incorporated herein by reference as if set forth in full herein. Since the filing of the patent application that led to the above noted patent, various papers about conformable contact mask plating (i.e. INSTANT MASKING) and electrochemical fabrication have been published:

(1) A. Cohen, G. Zhang, F. Tseng, F. Mansfeld, U. Frodis and P. Will, "EFAB: Batch production of functional, fully-dense metal parts with micro-scale features", Proc. 9th Solid Freeform Fabrication, The University of Texas at Austin, p161, August 1998.

(2) A. Cohen, G. Zhang, F. Tseng, F. Mansfeld, U. Frodis and P. Will, "EFAB: Rapid, Low-Cost Desktop Micromachining of High Aspect Ratio True 3-D MEMS", Proc. 12th IEEE Micro Electro Mechanical Systems Workshop, IEEE, p244, January 1999.

(3) A. Cohen, "3-D Micromachining by Electrochemical Fabrication", Micromachine Devices, March 1999.

(4) G. Zhang, A. Cohen, U. Frodis, F. Tseng, F. Mansfeld, and P. Will, "EFAB: Rapid Desktop Manufacturing of True 3-D Microstructures", Proc. 2nd International Conference on Integrated MicroNanotechnology for Space Applications, The Aerospace Co., April 1999.

(5) F. Tseng, U. Frodis, G. Zhang, A. Cohen, F. Mansfeld, and P. Will, "EFAB: High Aspect Ratio, Arbitrary 3-D Metal Microstructures using a Low-Cost Automated Batch Process", 3rd International Workshop on High Aspect Ratio MicroStructure Technology (HARMST'99), June 1999.

(6) A. Cohen, U. Frodis, F. Tseng, G. Zhang, F. Mansfeld, and P. Will, "EFAB: Low-Cost, Automated Electrochemical Batch Fabrication of Arbitrary 3-D Microstructures", Micromachining and Microfabrication Process Technology, SPIE 1999 Symposium on Micromachining and Microfabrication, September 1999.

(7) F. Tseng, G. Zhang, U. Frodis, A. Cohen, F. Marisfeld, and P. Will, "EFAB: High Aspect Ratio, Arbitrary 3-D Metal Microstructures using a Low-Cost Automated Batch Process", MEMS Symposium, ASME 1999 International Mechanical Engineering Congress and Exposition, November, 1999.

(8) A. Cohen, "Electrochemical Fabrication (EFAB™)", Chapter 19 of The MEMS Handbook, edited by Mohamed Gad-EI-Hak, CRC Press, 2002.

(9) Microfabrication—Rapid Prototyping's Killer Application", pages 1-5 of the Rapid Prototyping Report, CAD/CAM Publishing, Inc., June 1999.

The disclosures of these nine publications are hereby incorporated herein by reference as if set forth in full herein.

The electrochemical deposition process may be carried out in a number of different ways as set forth in the above patent and publications. In one form, this process involves the execution of three separate operations during the formation of each layer of the structure that is to be formed:

1. Selectively depositing at least one material by electrodeposition upon one or more desired regions of a substrate.
2. Then, blanket depositing at least one additional material by electrodeposition so that the additional deposit covers both the regions that were previously selectively deposited onto, and the regions of the substrate that did not receive any previously applied selective depositions.
3. Finally, planarizing the materials deposited during the first and second operations to produce a smoothed surface of a first layer of desired thickness having at least one region containing the at least one material and at least one region containing at least the one additional material.

After formation of the first layer, one or more additional layers may be formed adjacent to the immediately preceding layer and adhered to the smoothed surface of that preceding layer. These additional layers are formed by repeating the first through third operations one or more times wherein the formation of each subsequent layer treats the previously formed layers and the initial substrate as a new and thickening substrate.

Once the formation of all layers has been completed, at least a portion of at least one of the materials deposited is generally removed by an etching process to expose or release the three-dimensional structure that was intended to be formed.

The preferred method of performing the selective electrodeposition involved in the first operation is by conformable contact mask plating. In this type of plating, one or more conformable contact (CC) masks are first formed. The CC masks include a support structure onto which a patterned conformable dielectric material is adhered or formed. The conformable material for each mask is shaped in accordance with a particular cross-section of material to be plated. At least one CC mask is needed for each unique cross-sectional pattern that is to be plated.

The support for a CC mask is typically a plate-like structure formed of a metal that is to be selectively electroplated and from which material to be plated will be dissolved. In this typical approach, the support will act as an anode in an electroplating process. In an alternative approach, the support may instead be a porous or otherwise perforated material through which deposition material will pass during an electroplating operation on its way from a distal anode to a deposition surface. In either approach, it is possible for CC masks to share a common support, i.e. the patterns of conformable dielectric material for plating multiple layers of material may be located in different areas of a single support structure. When a single support structure contains multiple plating patterns, the entire structure is referred to as the CC mask while the individual plating masks may be referred to as "submasks". In the present application such a distinction will be made only when relevant to a specific point being made.

In preparation for performing the selective deposition of the first operation, the conformable portion of the CC mask is placed in registration with and pressed against a selected portion of the substrate (or onto a previously formed layer or onto a previously deposited portion of a layer) on which deposition is to occur. The pressing together of the CC mask and substrate occur in such a way that all openings, in the conformable portions of the CC mask contain plating solution. The conformable material of the CC mask that contacts the substrate acts as a barrier to electrodeposition while the openings in the CC mask that are filled with electroplating solution act as pathways for transferring material from an anode (e.g. the CC mask support) to the non-contacted portions of the substrate (which act as a cathode during the plating operation) when an appropriate potential and/or current are supplied.

An example of a CC mask and CC mask plating are shown in FIGS. 1A-1C. FIG. 1A shows a side view of a CC mask 8 consisting of a conformable or deformable (e.g. elastomeric) insulator 10 patterned on an anode 12. The anode has two functions. One is as a supporting material for the patterned insulator 10 to maintain its integrity and alignment since the pattern may be topologically complex (e.g., involving isolated "islands" of insulator material). The other function is as an anode for the electroplating operation. FIG. 1A also depicts a substrate 6 separated from mask 8. CC mask plating selectively deposits material 22 onto a substrate 6 by simply pressing the insulator against the substrate then electrodepositing material through apertures 26a and 26b in the insulator as shown in FIG. 1B. After deposition, the CC mask is separated, preferably non-destructively, from the substrate 6 as shown in FIG. 1C. The CC mask plating process is distinct from a "through-mask" plating process in that in a through-mask plating process the separation of the masking material from the substrate would occur destructively. As with through-mask plating, CC mask plating deposits material selectively and simultaneously over the entire layer. The plated region may consist of one or more isolated plating regions where these isolated plating regions may belong to a single structure that is being formed or may belong to multiple structures that are being formed simultaneously. In CC mask plating as individual masks are not intentionally destroyed in the removal process, they may be usable in multiple plating operations.

Another example of a CC mask and CC mask plating is shown in FIGS. 1D-1G. FIG. 1D shows an anode 12' separated from a mask 8' that includes a patterned conformable material 10' and a support structure 20. FIG. 1D also depicts substrate 6 separated from the mask 8'. FIG. 1E illustrates the mask 8' being brought into contact with the substrate 6. FIG. 1F illustrates the deposit 22' that results from conducting a current from the anode 12' to the substrate 6. FIG. 1G illustrates the deposit 22' on substrate 6 after separation from mask 8'. In this example, an appropriate electrolyte is located between the substrate 6 and the anode 12' and a current of ions coming from one or both of the solution and the anode are conducted through the opening in the mask to the substrate where material is deposited. This type of mask may be referred to as an anodeless INSTANT MASK™ (AIM) or as an anodeless conformable contact (ACC) mask.

Unlike through-mask plating, CC mask plating allows CC masks to be formed completely separate from the fabrication of the substrate on which plating is to occur (e.g. separate from a three-dimensional (3D) structure that is being formed). CC masks may be formed in a variety of ways, for example, a photolithographic process may be used. All masks can be generated simultaneously, e.g. prior to structure fabrication rather than during it. This separation makes possible a simple, low-cost, automated, self-contained, and internally-clean "desktop factory" that can be installed almost anywhere to fabricate 3D structures, leaving any required clean room processes, such as photolithography to be performed by service bureaus or the like.

An example of the electrochemical fabrication process discussed above is illustrated in FIGS. 2A-2F. These figures show that the process involves deposition of a first material 2 which is a sacrificial material and a second material 4 which is a structural material. The CC mask 8, in this example, includes a patterned conformable material (e.g. an elastomeric dielectric material) 10 and a support 12 which is made from deposition material 2. The conformal portion of the CC mask is pressed against substrate 6 with a plating solution 14 located within the openings 16 in the conformable material 10. An electric current, from power supply 18, is then passed through the plating solution 14 via (a) support 12 which doubles as an anode and (b) substrate 6 which doubles as a cathode. FIG. 2A illustrates that the passing of current causes material 2 within the plating solution and material 2 from the anode 12 to be selectively transferred to and plated on the substrate 6. After electroplating the first deposition material 2 onto the substrate 6 using CC mask , the CC mask 8 is removed as shown in FIG. 2B. FIG. 2C depicts the second deposition material 4 as having been blanket-deposited (i.e. non-selectively deposited) over the previously deposited first deposition material 2 as well as over the other portions of the substrate 6. The blanket deposition occurs by electroplating from an anode (not shown), composed of the second material, through an appropriate plating solution (not shown), and to the cathode/substrate 6. The entire two-material layer is then planarized to achieve precise thickness and flatness as shown in FIG. 2D. After repetition of this process for all layers, the multi-layer structure 20 formed of the second material 4 (i.e. structural material) is embedded in first material 2 (i.e. sacrificial material) as shown in FIG. 2E. The embedded structure is etched to yield the desired device, i.e. structure 20, as shown in FIG. 2F.

Various components of an exemplary manual electrochemical fabrication system 32 are shown in FIGS. 3A-3C.

The system 32 consists of several subsystems 34, 36, 38, and 40. The substrate holding subsystem 34 is depicted in the upper portions of each of FIGS. 3A-3C and includes several components: (1) a carrier 48, (2) a metal substrate 6 onto which the layers are deposited, and (3) a linear slide 42 capable of moving the substrate 6 up and down relative to the carrier 48 in response to drive force from actuator 44. Subsystem 34 also includes an indicator 46 for measuring differences in vertical position of the substrate which may be used in setting or determining layer thicknesses and/or deposition thicknesses. The subsystem 34 further includes feet 68 for carrier 48 which can be precisely mounted on subsystem 36.

The CC mask subsystem 36 shown in the lower portion of FIG. 3A includes several components: (1) a CC mask 8 that is actually made up of a number of CC masks (i.e. submasks) that share a common support/anode 22, (2) precision X-stage 54, (3) precision Y-stage 56, (4) frame 72 on which the feet 68 of subsystem 34 can mount, and (5) a tank 58 for containing the electrolyte 16. Subsystems 34 and 36 also include appropriate electrical connections (not shown) for connecting to an appropriate power source (not shown) for driving the CC masking process.

The blanket deposition subsystem 38 is shown in the lower portion of FIG. 3B and includes several components: (1) an anode 62, (2) an electrolyte tank 64 for holding plating solution 66, and (3) frame 74 on which feet 68 of subsystem 34 may sit. Subsystem 38 also includes appropriate electrical connections (not shown) for connecting the anode to an appropriate power supply (not shown) for driving the blanket deposition process.

The planarization subsystem 40 is shown in the lower portion of FIG. 3C and includes a lapping plate 52 and associated motion and control systems (not shown) for planarizing the depositions.

In addition to teaching the use of CC masks for electrodeposition purposes, the '630 patent also teaches that the CC masks may be placed against a substrate with the polarity of the voltage reversed and material may thereby be selectively removed from the substrate. It indicates that such removal processes can be used to selectively etch, engrave, and polish a substrate, e.g., a plaque.

The '630 patent further indicates that the electroplating methods and articles disclosed therein allow fabrication of devices from thin layers of materials such as, e.g., metals, polymers, ceramics, and semiconductor materials. It further indicates that although the electroplating embodiments described therein have been described with respect to the use of two metals, a variety of materials, e.g., polymers, ceramics and semiconductor materials, and any number of metals can be deposited either by the electroplating methods therein, or in separate processes that occur throughout the electroplating method. It indicates that a thin plating base can be deposited, e.g., by sputtering, over a deposit that is insufficiently conductive (e.g., an insulating layer) so as to enable subsequent electroplating. It also indicates that multiple support materials (i.e. sacrificial materials) can be included in the electroplated element allowing selective removal of the support materials.

The '630 patent additionally teaches that the electroplating methods disclosed therein can be used to manufacture elements having complex microstructure and close tolerances between parts. An example is given with the aid of FIGS. 14A-14E of that patent. In the example, elements having parts that fit with close tolerances, e.g., having gaps between about 1-5 um, including electroplating the parts of the device in an unassembled, preferably pre-aligned, state and once fabricated the individual parts can be moved into operational relation with each other or they can simply fall together. Once together the separate parts may be retained by clips or the like.

Another method for forming microstructures from electroplated metals (i.e. using electrochemical fabrication techniques) is taught in U.S. Pat. No. 5,190,637 to Henry Guckel, entitled "Formation of Microstructures by Multiple Level Deep X-ray Lithography with Sacrificial Metal layers". This patent teaches the formation of metal structure utilizing mask exposures. A first layer of a primary metal is electroplated onto an exposed plating base to fill a void in a photoresist, the photoresist is then removed and a secondary metal is electroplated over the first layer and over the plating base. The exposed surface of the secondary metal is then machined down to a height which exposes the first metal to produce a flat uniform surface extending across the both the primary and secondary metals. Formation of a second layer may then begin by applying a photoresist layer over the first layer and then repeating the process used to produce the first layer. The process is then repeated until the entire structure is formed and the secondary metal is removed by etching. The photoresist is formed over the plating base or previous layer by casting and the voids in the photoresist are formed by exposure of the photoresist through a patterned mask via X-rays or UV radiation.

The '637 patent teaches the locating of a plating base onto a substrate in preparation for electroplating materials onto the substrate. The plating base is indicated as typically involving the use of a sputtered film of an adhesive metal, such as chromium or titanium, and then a sputtered film of the metal that is to be plated. It is also taught that the plating base may be applied over an initial sacrificial layer of material on the substrate so that the structure and substrate may be detached if desired. In such cases after formation of the structure the plating base may be patterned and removed from around the structure and then the sacrificial layer under the plating base may be dissolved to free the structure. Substrate materials mentioned in the '637 patent include silicon, glass, metals, and silicon with protected processed semiconductor devices. A specific example of a plating base includes about 150 angstroms of titanium and about 300 angstroms of nickel, both of which are sputtered at a temperature of 160° C. In another example it is indicated that the plating base may consist of 150 angstroms of titanium and 150 angstroms of nickel where both are applied by sputtering.

Electrochemical Fabrication provides the ability to form prototypes and commercial quantities of miniature objects, parts, structures, devices, and the like at reasonable costs and in reasonable times. In fact, Electrochemical Fabrication is an enabler for the formation of many structures that were hitherto impossible to produce. Electrochemical Fabrication opens the spectrum for new designs and products in many industrial fields. Even though Electrochemical Fabrication offers this new capability and it is understood that Electrochemical Fabrication techniques can be combined with designs and structures known within various fields to produce new structures, certain uses for Electrochemical Fabrication provide designs, structures, capabilities and/or features not known or obvious in view of the state of the art.

A need exists in various fields for miniature devices having improved characteristics, reduced fabrication times, reduced fabrication costs, simplified fabrication processes, greater versatility in device design, improved selection of materials, improved material properties, more cost effective and less risky production of such devices, and/or more independence between geometric configuration and the selected fabrication process.

There is a need, particularly for minimally-invasive surgery, for a small instrument that can quickly ablate, i.e. remove, sizeable volumes of tissue a) without needing to remove the entire instrument along with each piece of tissue; b) while ensuring that the removed tissue is transported away from the donor site; c) in some cases, while ensuring that excised tissue (e.g., if cancerous) is fully captured and not lost; and d) in some cases, while ensuring that each discrete element or piece of tissue removed is of a small enough size to ensure that only selected tissue is removed.

SUMMARY OF THE INVENTION

It is an object of some embodiments of the invention to provide an improved method and apparatus for mechanically cutting away small volumes of material and potentially for capturing the material.

It is an object of some embodiments of the invention to provide an improved method and apparatus for mechanically cutting away small volumes of material from a patient's body during a minimally invasive surgical procedure and for removing the material. In some variations of this object material may be removed in a continuous manner without removing the tool from the body of the patient. In some variations of this object material is captured in a continuous series of small volumes, samples, or bites and each bite is held separate from the other bites and even the order of sampling is preserved.

Other objects and advantages of various aspects and embodiments of the invention will be apparent to those of skill in the art upon review of the teachings herein. The various aspects of the invention, set forth explicitly herein or otherwise ascertained from the teachings herein, may address one or more of the above objects alone or in combination, or alternatively may address some other object ascertained from the teachings herein. It is not necessarily intended that all objects be addressed by any single aspect of the invention even though that may be the case with regard to some aspects.

A first aspect of the invention provides a medical instrument for removing small specimens of tissue from a patient's body during a minimally invasive surgical procedure, including: (a) an elongated housing having a distal end and a proximal end; (b) an inlet to the housing located near the distal end of the housing; (c) two rotary elements supported directly or indirectly by the housing, one of which is located near the distal end of the housing and the other which is located closer away from the distal end of the housing; (d) an elongated flexible or bendable element extending around the rotary elements which may move in a desired direction by an activation mechanism; and (e) a plurality of anvils located on the elongated flexible or bendable member or on the distally located rotary element, such that when the elongated flexible or bendable element is moved, the anvils in turn rotate past the at least one opening, and such that when tissue is located in the inlet at least a portion of it is removed by the interaction of the anvil with an edge of the housing, wherein the removed tissue is transported away from the inlet, within the housing toward the proximal end of the housing.

Other aspects of the invention will be understood by those of skill in the art upon review of the teachings herein. Other aspects of the invention may involve combinations of the above noted aspects of the invention. These other aspects of the invention may provide various combinations of the aspects presented above as well as provide other configurations, structures, functional relationships, and processes that have not been specifically set forth above.

BRIEF DESCRIPTION OF THE DRAWINGS

FIG. 5A provides a perspective view, from above, of an open version of an exemplary instrument while

DETAILED DESCRIPTION OF PREFERRED EMBODIMENTS OF THE INVENTION

Fabrication Methods

FIGS. 1A-1G, 2A-2F, and 3A-3C illustrate various features of one form of electrochemical fabrication that are known. Other electrochemical fabrication techniques are set forth in the '630 patent referenced above, in the various previously incorporated publications, in various other patents and patent applications incorporated herein by reference, still others may be derived from combinations of various approaches described in these publications, patents, and applications, or are otherwise known or ascertainable by those of skill in the art from the teachings set forth herein. All of these techniques may be combined with those of the various embodiments of various aspects of the invention to yield enhanced embodiments. Still other embodiments may be derived from combinations of the various embodiments explicitly set forth herein.

Figure 1A:
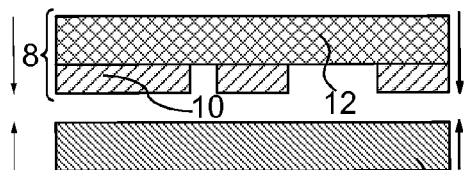
FIGS. 1A-1C schematically depict side views of various stages of a CC mask plating process, while FIGS. 1D-G schematically depict a side views of various stages of a CC mask plating process using a different type of CC mask.
Figure 1B:
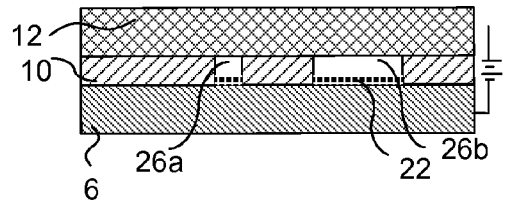
Figure 1C:
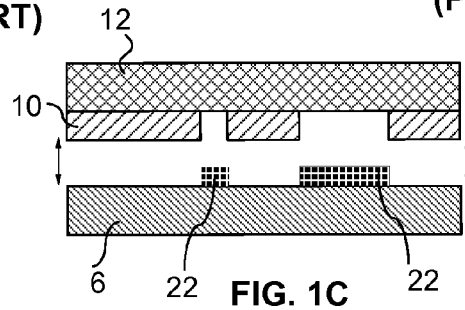
Figure 1D:
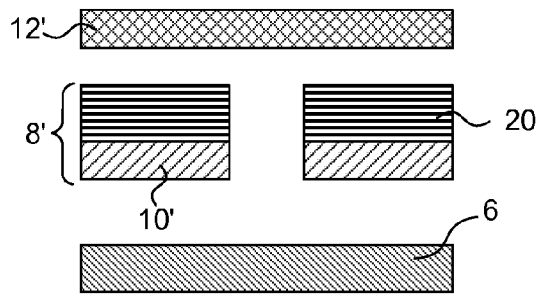
Figure 1E:
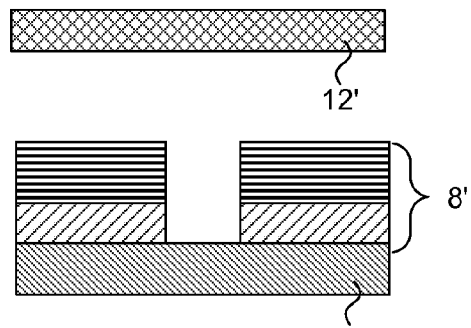
Figure 1F:
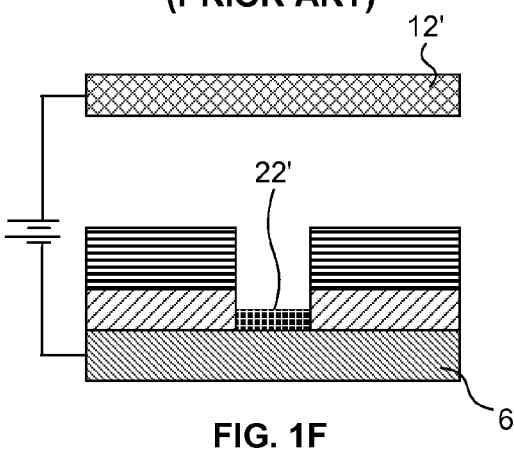
Figure 1G:
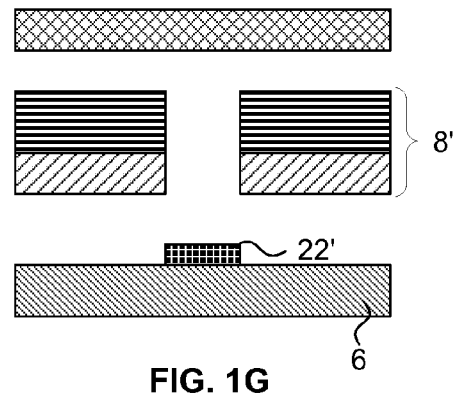
Figure 2A:
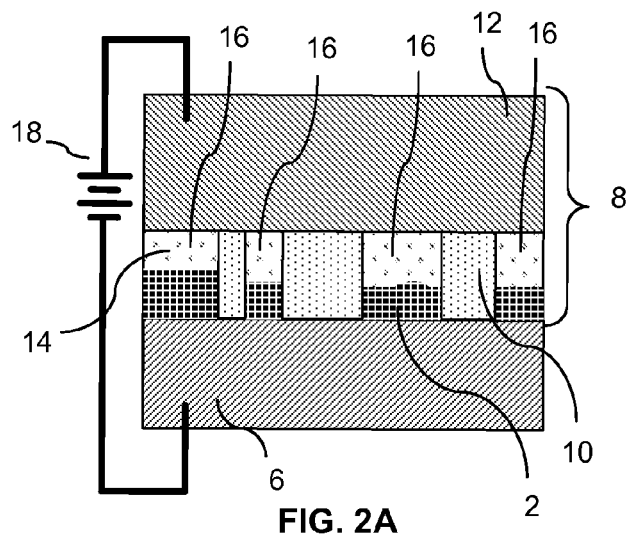
FIGS. 2A-2F schematically depict side views of various stages of an electrochemical fabrication process as applied to the formation of a particular structure where a sacrificial material is selectively deposited while a structural material is blanket deposited.
Figure 2B:
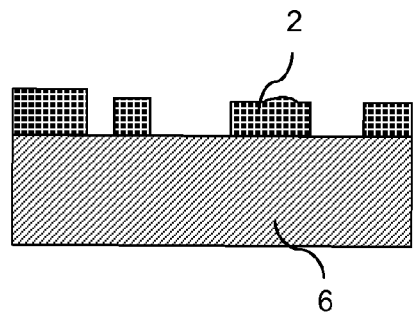
Figure 2C:
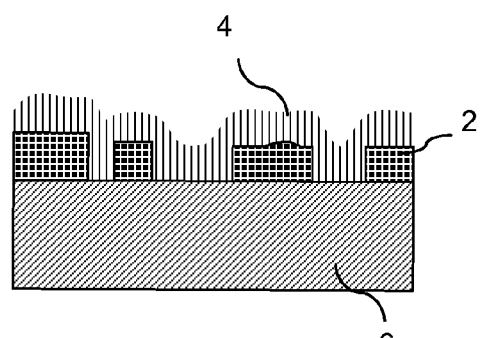
Figure 2D:
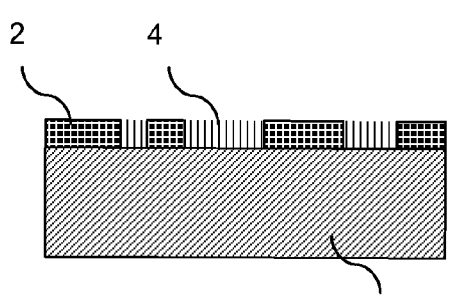
Figure 2E:
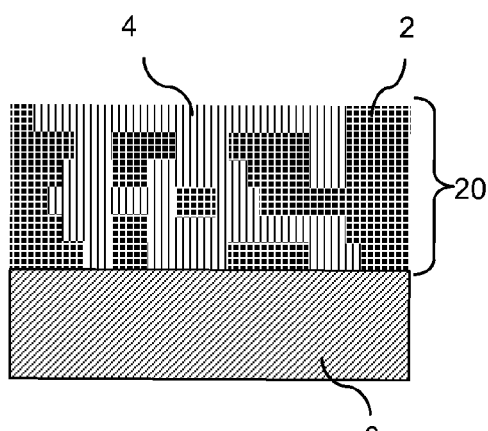
Figure 2F:
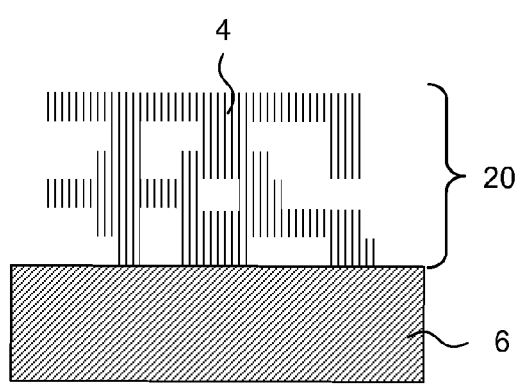
Figure 3A:
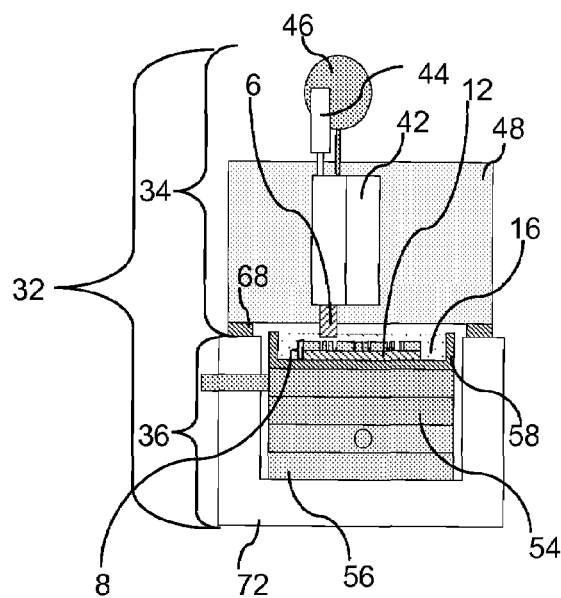
FIGS. 3A-3C schematically depict side views of various example subassemblies that may be used in manually implementing the electrochemical fabrication method depicted in FIGS. 2A-2F.
Figure 3B:
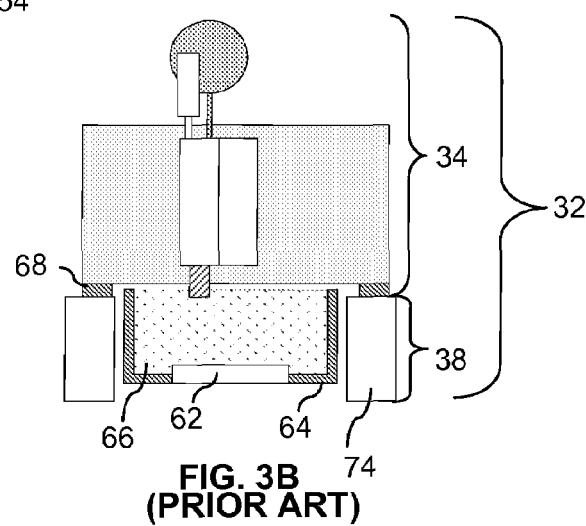
Figure 3C:
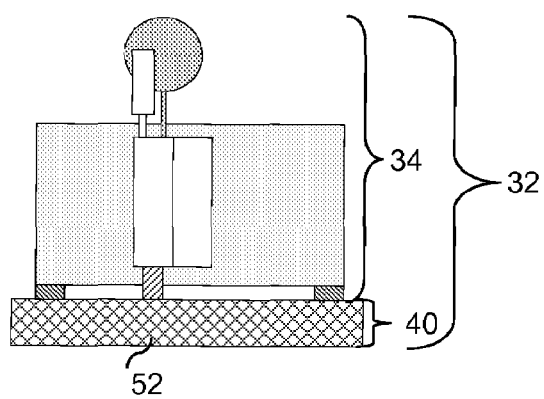
Figure 4A:
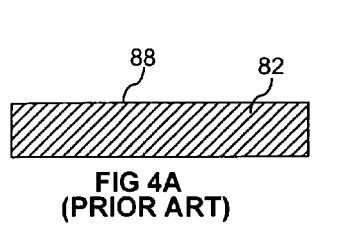
FIGS. 4A-4F schematically depict the formation of a first layer of a structure using adhered mask plating where the blanket deposition of a second material overlays both the openings between deposition locations of a first material and the first material itself
Figure 4B:
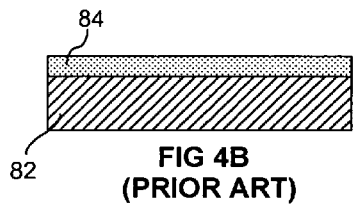
Figure 4C:
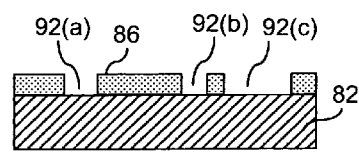
Figure 4D:
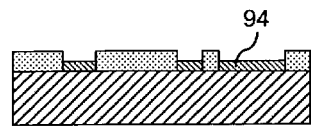
Figure 4E:
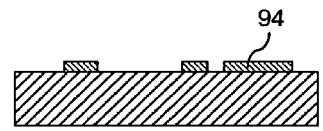
Figure 4F:
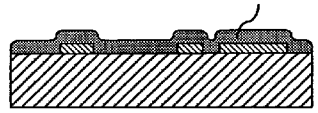
Figure 4G:
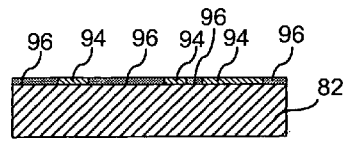
FIG. 4G depicts the completion of formation of the first layer resulting from planarizing the deposited materials to a desired level.
Figure 4H:
FIGS. 4H and 4I respectively depict the state of the process after formation of the multiple layers of the structure and after release of the structure from the sacrificial material.
Figure 4I:
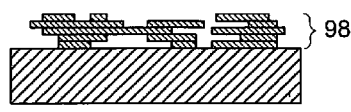

FIGS. 4A-4GI illustrate various stages in the formation of a single layer of a multi-layer fabrication process where a second metal is deposited on a first metal as well as in openings in the first metal so that the first and second metal form part of the layer. In FIG. 4A a side view of a substrate 82 is shown, onto which patternable photoresist 84 is cast as shown in FIG. 4B. In FIG. 4C, a pattern of resist is shown that results from the curing, exposing, and developing of the resist. The patterning of the photoresist 84 results in openings or apertures 92(a)-92(c) extending from a surface 86 of the photoresist through the thickness of the photoresist to surface 88 of the substrate 82. In FIG. 4D a metal 94 (e.g. nickel) is shown as having been electroplated into the openings 92(a)-92(c). In FIG. 4E the photoresist has been removed (i.e. chemically stripped) from the substrate to expose regions of the substrate 82 which are not covered with the first metal 94. In FIG. 4F a second metal 96 (e.g. silver) is shown as having been blanket electroplated over the entire exposed portions of the substrate 82 (which is conductive) and over the first metal 94 (which is also conductive). FIG. 4G depicts the completed first layer of the structure which has resulted from the planarization of the first and second metals down to a height that exposes the first metal and sets a thickness for the first layer. In FIG. 4H the result of repeating the process steps shown in FIGS. 4B-4G several times to form a multi-layer structure are shown where each layer consists of two materials. For most applications, one of these materials is removed as shown in FIG. 4I to yield a desired 3-D structure 98 (e.g. component or device).

Some embodiments of the invention are directed to formation of three-dimensional structures from materials some of which may be electrodeposited or electroless deposited. These structures are formed from a plurality of layers each including at least two materials (e.g. 2 or more layers, more preferably five or more layers, and most preferably ten or more layers). In some embodiments structures having features positioned with micron level precision and minimum features size on the order of tens of microns are to be formed. In other embodiments structures with less precise feature placement and/or larger minimum features may be formed. In still other embodiments, higher precision and smaller minimum feature sizes may be desirable.

In some embodiments, alternatives, and techniques disclosed herein may form multi-layer structures using a single patterning technique on all layers or using different patterning techniques on different layers. For example, Various embodiments of the invention may perform selective patterning operations using conformable contact masks and masking operations (i.e. operations that use masks which are contacted to but not adhered to a substrate), proximity masks and masking operations (i.e. operations that use masks that at least partially selectively shield a substrate by their proximity to the substrate even if contact is not made), non-conformable masks and masking operations (i.e. masks and operations based on masks whose contact surfaces are not significantly conformable), and/or adhered masks and masking operations (masks and operations that use masks that are adhered to a substrate onto which selective deposition or etching is to occur as opposed to only being contacted to it). Adhered mask may be formed in a number of ways including (1) by application of a photoresist, selective exposure of the photoresist, and then development of the photoresist, (2) selective transfer of pre-patterned masking material, and/or (3) direct formation of masks from computer controlled depositions of material.

Patterning operations may be used in selectively depositing material and/or may be used in the selective etching of material. Selectively etched regions may be selectively filled in or filled in via blanket deposition, or the like, with a different desired material. In some embodiments, the layer-by-layer build up may involve the simultaneous formation of portions of multiple layers. In some embodiments, depositions made in association with some layer levels may result in depositions to regions associated with other layer levels. Such use of selective etching and interlaced material deposited in association with multiple layers is described in U.S. patent application Ser. No. 10/434,519, by Smalley, and entitled "Methods of and Apparatus for Electrochemically Fabricating Structures Via Interlaced Layers or Via Selective Etching and Filling of Voids layer elements" which is hereby incorporated herein by reference as if set forth in full.

In some embodiments structures may be formed a nickel-cobalt alloy (e.g. 80% nickel and 20% cobalt) while in other embodiments structures may be formed from a nickel-phosphor alloy, a nickel-titanium alloy, or other metal or metal alloy. In some embodiments, non metallic elements and/or non-conductive elements may be included in the structure. In some embodiments. More information about building structures from nickel-titanium alloys and other non-platable materials is provided in U.S. patent application Ser. No. 11/478,934, filed Jun. 29, 2006, by Cohen et al., and entitled "Electrochemical Fabrication Processes Incorporating Non-Platable Metals and/or Metals that are Difficult to Plate On". This referenced application is hereby incorporated herein by reference.

In some embodiments, structures may be formed directed from the build up of a plurality of layers where each layer is adhered to previously formed layers during its formation while in other embodiments, portions of the structure may be formed separately and then bonded together after their formation. In other embodiments, structures may be formed from processes that do not involve the formation and simultaneous adhesion of materials deposited on successively formed layers.

In the present application the following terms are generally intended to have the following definitions though the meaning of particular terms as used in particular contexts may vary from these definitions if the context makes it clear what the term is intended to mean in that circumstance.

The terms "three-dimensional structure", "structure", "part", "component", "device", and the like refer generally to intended or actually fabricated three-dimensional configurations (e.g. of structural material or materials) that are intended to be used for a particular purpose. Such structures, etc. may, for example, be designed with the aid of a three-dimensional CAD system. In some embodiments such structures will be formable from a plurality of adhered layers. When designing such structures, for example, the formation process that will be used in fabricating the structure may or may not be taken into consideration. For example, if the structure is to be formed from a plurality of adhered layers, it may be desirable to take into consideration the vertical levels that define layer transitions so that structural features are precisely located at layer boundary levels. The structures may be designed with sloping sidewalls or with vertical sidewalls. In designing such three-dimensional structures they may be designed in a positive manner (i.e. features of the structure itself defined) or in a negative manner (i.e. regions or features of sacrificial material within a build volume defined), or as a combination of both.

The terms "build axis" or "build orientation" refer to a direction that is generally perpendicular to the planes of layers from which a three-dimensional structure is formed and it points in the direction from previously formed layers to successively formed layers. The build orientation will generally be considered to extend in the vertical direction regardless of the actual orientation with respect to gravity of the build axis during layer formation (e.g. regardless of whether the direction of layer stacking is horizontal relative to the earth's gravity, upside down relative to gravity, or at some other angle relative to the earth's gravity).

The term "structural material" shall generally refer to one or more particular materials that are deposited during formation of one or more build layers at particular lateral positions, where the material is generally intended to form part or all of a final three-dimensional structure and where thicknesses of the particular material associated with one or more particular layers is typically substantially that of the thickness of that layer or the thicknesses of those layers. During formation of particular layers, structural material thickness may vary from the layer thicknesses by generally relative thin adhesion layer thicknesses, seed layer thicknesses, barrier layer thicknesses, or the like, or at edges of features where sloping sidewalls may exist. In some embodiments, the structural material associated with particular layers may be formed from a plurality of distinctly deposited materials whose combination defines an effective structural material.

The term "sacrificial material" shall generally refer to one or more particular materials that are deposited during formation of one or more build layers at particular lateral positions, where the material is generally intended to be removed from a final three-dimensional structure prior to putting it to its intended use. Sacrificial material does not generally refer to masking materials, or the like, that are applied during formation of a particular layer and then removed prior to the completion of formation of that layer. Sacrificial material or materials generally forms a portion of a plurality of build layers and are separated from structural material after formation of a plurality of layers (e.g. after completion of formation of all build layers). Some portion of a sacrificial material may become a pseudo structural material if it is completely encapsulated or effectively trapped by structural material such that it is not removed prior to putting the structure to use. For example, a copper sacrificial material may be intentionally encapsulated by a structural material (e.g. nickel or a nickel alloy) so as to improve thermal conductive or electrical conductive of the structure as a whole. The thicknesses of a particular sacrificial material associated with one or more particular layers is typically substantially that of the thickness of that layer or the thicknesses of those layers. During formation of particular layers, sacrificial material thickness may vary from the layer thicknesses by generally relative thin adhesion material thicknesses, seed material thicknesses, barrier material thicknesses, or the like, or at edges of features where sloping sidewalls may exist. In some embodiments, the sacrificial material associated with particular layers may be formed from a plurality of distinctly deposited material whose combination defines an effective sacrificial material.

The term "build layer", "structural layer", or simply "layer" generally refers to materials deposited within a build volume located between two planes spaced by a "layer thickness" along the build axis where at least one structural material exists in one or more lateral positions and at least one sacrificial material exists in one or more other lateral positions. During fabrication, build layers are generally stacked one upon another but in some embodiments, it is possible that build layers will be separated one from another, in whole or in part, by relative thin coatings of adhesion layer material, seed layer material, barrier layer material, or the like.

The term "layer thickness" is the height along the build axis between a lower boundary of a build layer and an upper boundary of that build layer. Layer thicknesses, for example may be in the two micron to fifty micron range, with ten micron to 30 micron being common. In some embodiments layer thicknesses may be thinner than 2 microns or thicker than 50 microns. In many embodiments, deposition thickness (i.e. the thickness of any particular material after it is deposited) is generally greater than the layer thickness and a net deposit thickness is set via one or more planarization processes which may include, for example, mechanical abrasion (e.g. lapping, fly cutting, polishing, grinding, and the like) and/or chemical etching (e.g. using selective or non-selective etchants). The lower boundary and upper boundary for a build layer may be set and defined in different ways. From a design point of view they may be set based on a desired vertical resolution of the structure (which may vary with height). From a data manipulation point of view, the vertical layer boundaries may be defined as the vertical levels at which data descriptive of the structure is processed or the layer thickness may be defined as the height separating successive levels of cross-sectional data that dictate how the structure will be formed. From a fabrication point of view, depending on the exact fabrication process used, the layer boundaries may be defined in a variety of different ways. For example by planarization levels or effective planarization levels (e.g. lapping levels, fly cutting levels, chemical mechanical polishing levels, mechanical polishing levels, vertical positions of structural and/or sacrificial materials after relatively uniform etch back following a mechanical or chemical mechanical planarization process). For example, by levels at which process steps or operations are repeated. At levels at which, at least theoretically, lateral extends of structural material can be changed to define new cross-sectional features of a structure.

The terms "adhesion layer", "seed layer", "barrier layer", and the like refer to coatings of one or more materials that are thin in comparison to the layer thickness (e.g. less than 20% of the layer thickness, more preferably less than 10% of the layer thickness, and even more preferably less than 5% of the layer thickness). Such coatings may be applied uniformly over a previously formed layer, they may be applied over a portion of a previously formed layer and over patterned structural or sacrificial material existing on a current layer so that a non-planar seed layer results, or they may be selectively applied to only certain locations on a previously formed layer. In the event such coatings are non-selectively applied they may be partially removed (1) prior to depositing either a sacrificial material or structural material as part of a current layer or (2) prior to beginning formation of the next layer or they may remain in place through the layer build up process and then etched away after formation of a plurality of layers where the thinness of the coating may be relied on so that undercutting of structural material on two consecutive layers is not excessive and/or where thinness of the coatings may be relied on for their destructive removal between regions of sacrificial material located on successive layers. More information about the formation of structures using non-planar seed layers is provided in U.S. patent application Ser. No. 10/841,300, filed May 7, 2004, by Lockard et al., and entitled "Methods for Electrochemically Fabrication Structures Using Adhered Masks, Incorporating Dielectric Sheets, and/or Seed Layers that are Partially Removed Via Planarization". This referenced application is incorporated herein by reference as if set forth in full herein.

The term "structural layer" shall refer to one or more structural materials deposited during formation of a particular build layer or to the configuration of such material within the lower and upper boundaries of the layer.

The term "sacrificial layer" shall refer to the one or more sacrificial materials deposited during formation of a particular build layer or to the configuration of such material within the lower and upper boundaries of the layer.

Tool Structure

Some embodiments of the invention combine aspects of both a Kerrison bone punch and chainsaw, such that tissue can be ablated in a continuous manner. In the exemplary design shown in the figures, the instrument measures approximately 22 mm in length, 3 mm in width, and 1 mm in height. Shorter versions are possible. Longer versions are possible, e.g., to allow transportation of specimens over larger distances or the accumulation of larger numbers of specimens. In the design shown, roughly cubic parcels of tissue about ⅓ mm on a side are removed (depending on how much material is fed into the opening with each 'nibble' of the instrument, as produced, for example, by a reciprocating motion of the actuation slide. The instrument allows for single, slow, controlled mechanical ablation, or removal, one nibble at a time. By motorizing the actuation slide, in some alternative embodiments, using a linear actuator and by providing a suction, air pressure, or other means for removing ablated material, or by instead directly driving a pulley having sprockets (e.g. using a chain of somewhat different design) along with removal means high rates of ablation (e.g., 1 cubic mm/second) can be achieved. Although manual reciprocating motion that actuates the instrument to produce one or a few parcels at a time is described here, both modes of operation are possible. If the instrument is motorized, then the motor speed may be continuously varied according to circumstances.

The exemplary instrument described in association with the figures is intended to remove tissue in lieu of more conventional instruments such as forceps, graspers, scalpels, curettes, punches, etc. Most of these instruments are unable to extract more than a single specimen at one time, after which they must be removed from the body in order to retrieve the specimen. Even those which may be capable of obtaining more than a single specimen do not reliably transport it over a significant distance and/or do not reliably capture the specimens without loss in the body or elsewhere.

Potential applications of the exemplary instrument in different embodiments include the following:

Multiple biopsy. Tissue specimens are excised in a particular order, one at a time, and retained within the instrument (the design shown has a capacity for holding about 50 samples) in the order obtained, thus allowing multiple specimens to be quickly obtained from different donor sites within a patient, with the location of the site recorded by the operator, and later correlated to the particular specimen. In some alternative embodiments of the invention, the instrument is provided with sensors (e.g., electromagnetic, optical, ultrasonic, mechanical) which measure the position of the instrument's inlet within the body, allowing position-based biopsy data to be easily obtained. In some other alternative embodiments, the instrument is provided with one or more identifiable tags that may be detected using sensors located outside the patient's body such that positioning of the instrument may be precisely known and correlated to the activity of the instrument.

Precise yet rapid tumor resection. Small regions of tumor tissue can be removed precisely, one parcel or bite at a time, e.g., from the region between the tumor and healthy tissue. For regions far from healthy tissue and especially for large tumors, the speed can be dramatically increased. Resection of brain tumors is one application. If the instrument is non-magnetic, then MRI-guided procedures (to visualize tumor extents) are possible.

Ablation of fetal heart tissue. If miniaturized sufficiently to allow delivery of the instrument through a small needle through the uterus, tissue may be removed from the walls and valve surfaces of the fetal heart with the goal of treating conditions prenatally (e.g., preventing hypoplastic left heart syndrome).

General ablation/resection. Removal of abnormal muscle, scar tissue, fat, bone (with a sufficiently-robust device), and other tissue may be carried out with the instrument. The instrument may be used somewhat like a saw or knife to cut through tissue.

An exemplary embodiment of the instrument and various alternatives are described herein in conjunction with the illustrations of FIGS. 5-21. The following description focuses primarily on two variations of the exemplary instrument. In the first, the instrument is designed in an open configuration which both facilitates release of sacrificial material and enables individual, ordered retrieval of specimens. In the second, the instrument is designed in a closed version which does not require assembly and which delivers specimens to a discharge port. A number of release holes may be seen in both versions, to facilitate release of sacrificial material which may be used in the fabrication of the instrument; however, the closed version has more of these.

Figure 5A:
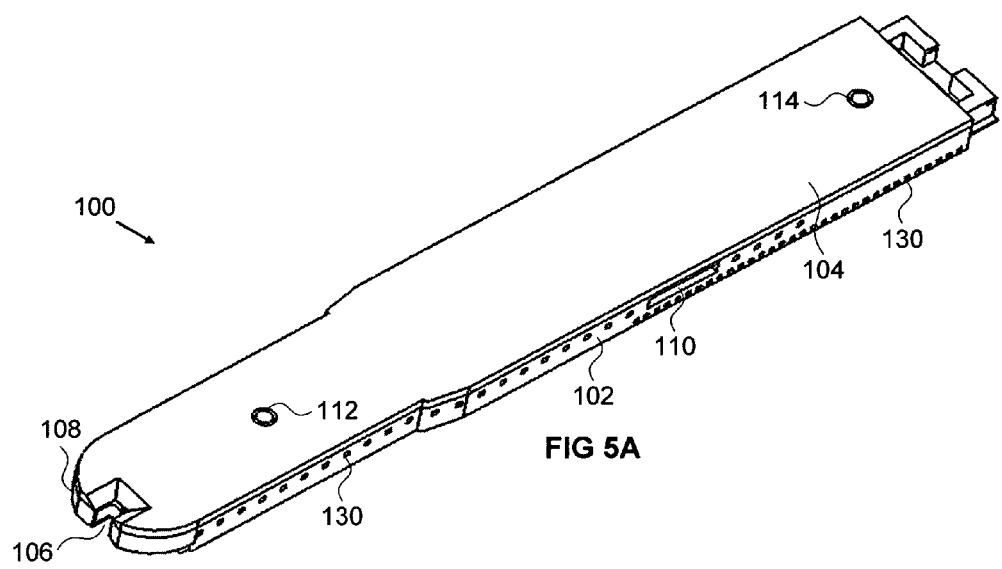
Figure 5B:
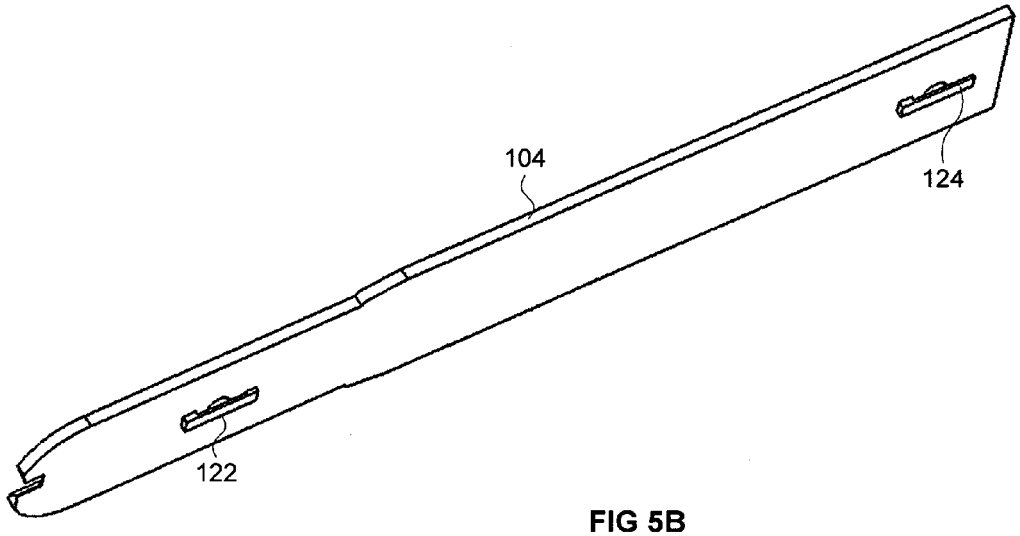
FIG. 5B shows the underside of the lid that forms part of the instrument of FIG. 5A.

FIG. 5A provides a perspective view, from above, of the open version of the exemplary instrument 100 with its lid 104 attached to main body 102. Of note is the tissue inlet 106 at the distal end 108 of the instrument, and distal button 112 and proximal button 114 on lid 104 that are used when installing and removing lid 104 from the rest of the instrument 100. Also visible is slot 110 for allowing captured tissue to be released from the instrument and release holes 130. FIG. 5B shows the lid 104 from the underside, which allows both distal lid catch 122 and proximal lid catch 124 to be seen.

Figure 6A:
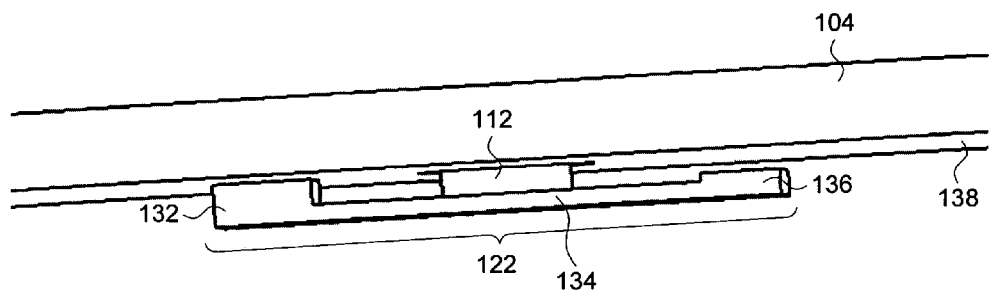
FIG. 6A provides a perspective view showing the distal lid catch of the lid of FIG. 5B in detail.

FIG. 6A shows the distal lid catch 122 in detail. It includes a base 132 that connects the lid catch 122 to lid 104, cantilever 134 which holds button 112 and catch protrusion 136. Cantilever 134 provides an elastic element that allows protrusion 136 to be moved away from the underside 138 of lid 134 by depressing button 112 and to return protrusion back to its original position when button 112 is released. Protrusion 136 and latch with ledge protrusion 146 (as seen in FIG. 6B) which forms part of the main body 102 of instrument 100.

Figure 6B:
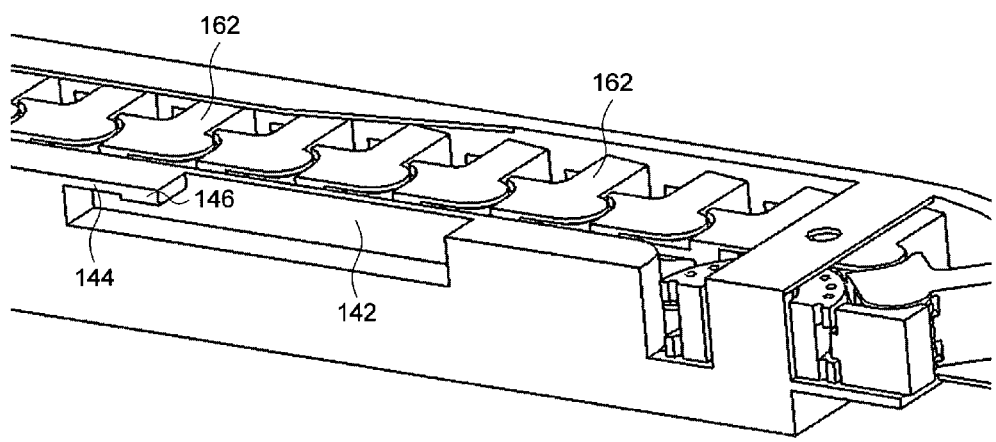
FIG. 6B provides a perspective view showing the ledge protrusions that is to engage the distal lid catch of FIG. 6A FIG. 7A provides a perspective view of the main body of the instrument of FIG. 5A while FIG. 7B provides a close up view of the distal and middle portions of the main body of the instrument with the various caps removed so that the chain links and pulleys can be more clearly seen.

FIG. 6B shows the distal end of the left side (while looking along the length of the instrument from the proximal end to the distal end) of the main body 102 of the open version of the instrument 100 with lid 104 removed. In this figure, ledge protrusion 146 and distal lid catch slot ledge 144 can be seen. When the lid 104 and main body 102 are located in their joined positions, catch protrusion 136 sits against ledge 144 and is held in place by ledge protrusion 146 thus causing the lid 104 and main body to be fixed together. In other embodiments additional mechanisms or other mechanisms may be used to retain the main body and lid components in appropriate relative positions.

Figure 7A:
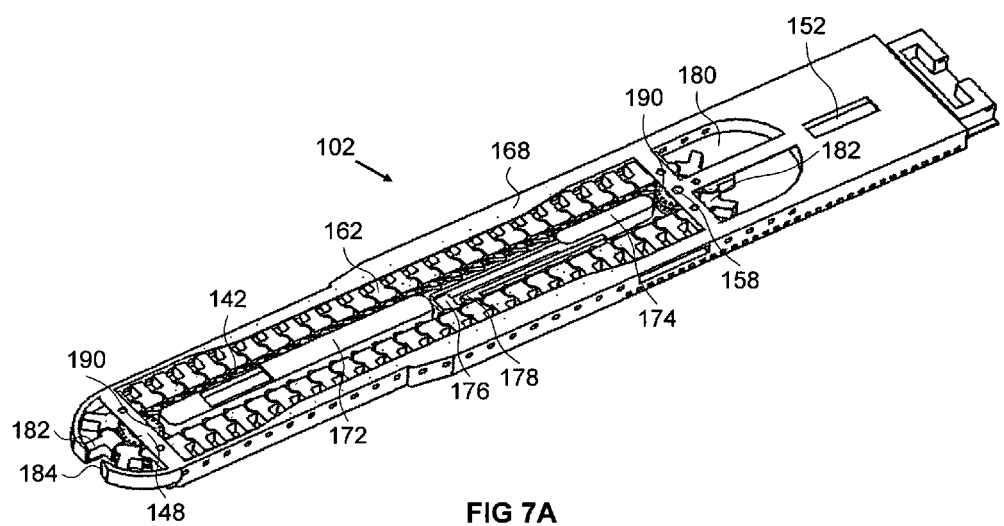
Figure 7B:
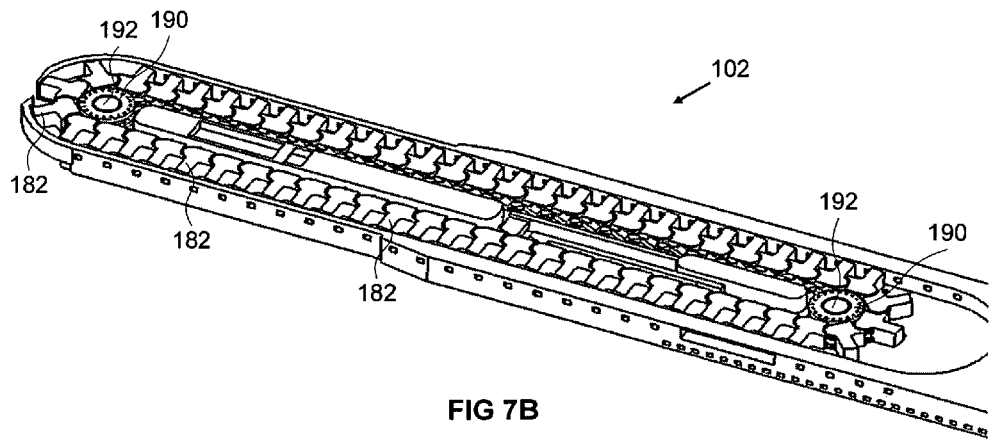

The proximal end of the main body 102 has a similar slot for receiving the proximal lid catch. The proximal lid catch may be the same as the distal catch, or may lack the protrusion, as is the case here. In alternative embodiments, the catch that includes the protrusion may be the proximal catch. In this case of a single catch only one button (the one that triggers the catch with the protrusion) needs to be depressed for removal of the lid. The lid is placed onto the body of the instrument such that the two catches fall into their respective slots. The buttons are then depressed, flexing the cantilevers and allowing the lid to be slid proximally. When the lid has moved sufficiently, the distal catch protrusion engages the distal ledge protrusion, preventing the lid from sliding out until the distal button is pressed. Even if no protrusions are provided proximally, depressing the proximal button may be required just to provide sufficient clearance between the cantilever and the ledge to allow the lid to slide. In alternative embodiments, other mechanism FIG. 7A provides a perspective view of the main body 102 of the instrument 100 while FIG. 7B provides a close up view of the distal and middle portions of the main body of the instrument with the various caps removed so that the chain links and pulleys can be more clearly seen. Visible are the chain of links 162, both catch slots 142 and 152, distal pulley cap 148, proximal pulley cap 158, and chain cap 168 which are used to retain the distal and proximal pulleys and the chain. Also visible is the proximal end of actuation slide 164 to which a cable, rod, or other connection may be made for actuating movement of the chain. Distal and proximal stiffeners 172 and 174 are also visible along with retainer head 176, pawl head 178, and cavity 180, among other features. The links 162 are equipped with anvils 182, which can be used to force tissue against cutting edge 184. Each link 162 is connected to adjacent links so that a continuous, closed chain is formed. Pulley caps 148 and 158 prevent their respective pulleys. 190 from coming off their shafts 192, and along with cap 168, prevent the chain coming off the pulleys 190 prior to tensioning of the chain (which will be described hereafter). The stiffeners 172 and 174 increase the bending stiffness of the instrument 100. The retainer head 176 and pawl head 178 are used to move the chain when the actuation slide interface is reciprocated. Finally, the cavity 180 provides room for the proximal pulley when the chain is stretched, and provides a reservoir for specimens if the number of bites made prior to removing the instrument exceed the number of gaps between links along one side of the instrument (this assumes that the specimens are not removed from slot 110 or that slot 110 is removed). In some alternative embodiments, an enclosure may be provided within the gap so that removed tissue may be retained within the gaps between individual chain links as additional bites are taken such that the capacity of the instrument to retain the sequence of samples may be enhanced to nearly the full length of the chain as opposed to less that half the length of the chain in the current exemplary embodiment.

Figure 8:
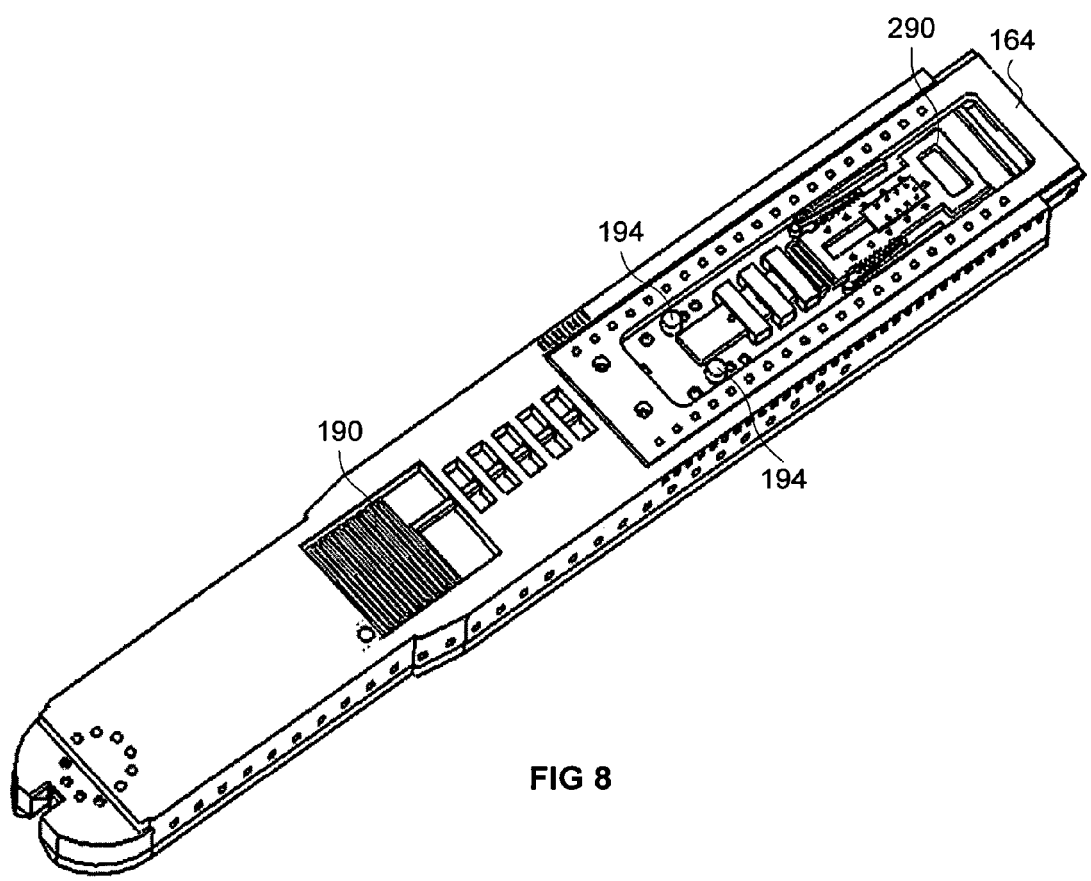
FIG. 8 provides a perspective view of the main body of the instrument of FIG. 5A from the bottom.

FIG. 8 provides a perspective view of the main body 102 of instrument 100 from the bottom. Visible is the actuation slide 164 which advances the chain when reciprocated; two stops 194 for the actuation slide to prevent excessive travel; a pawl return spring 190, which returns the pawl to its distal position when the actuation slide 164 is released; and a tensioning loop 192 which may be pulled to cause tensioning of the chain links against the pulleys.

Figure 9A:
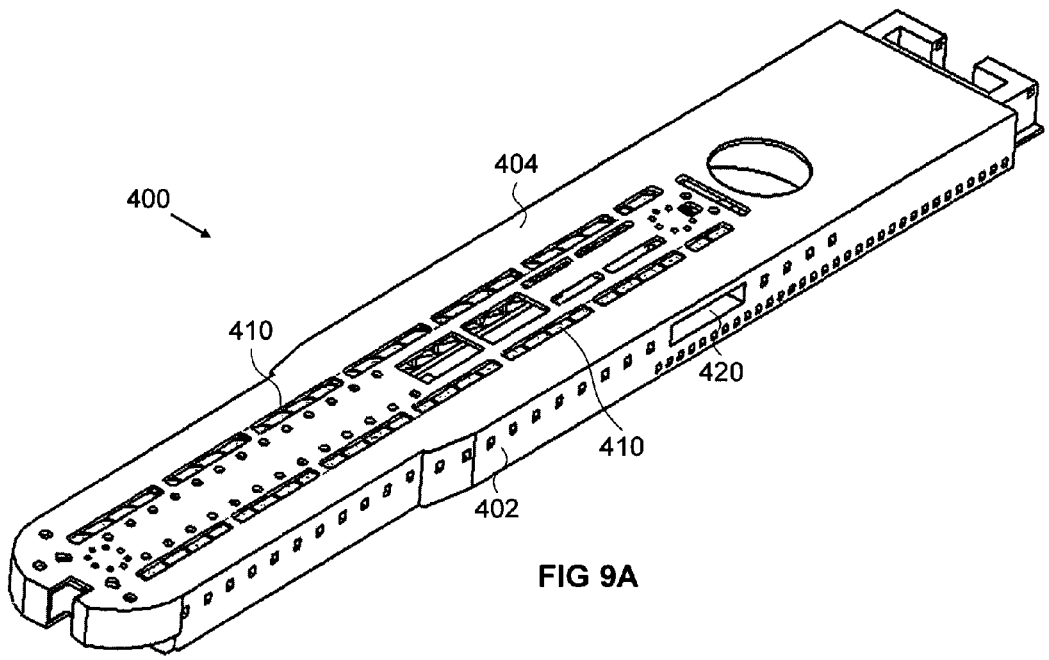
FIG. 9A provides a perspective view of a second exemplary embodiment which is lidless, or closed version, of the embodiment of FIG. 5A.

FIG. 9A provides a perspective view of an instrument 400 (i.e. the closed version) which is similar to instrument 100 with the exception that the separate lid 104 of instrument 100 is replaced by a modified main body 402, as compared to main body 102, that includes a top 404 with sacrificial material release holes 410. This version is also provided with a discharge port 420 such that tissue can be removed. In some alternative embodiments, the discharge port may be located on the other side of the instrument to allow the instrument to capture more tissue sample prior to the samples reaching the discharge port.

Figure 9B:
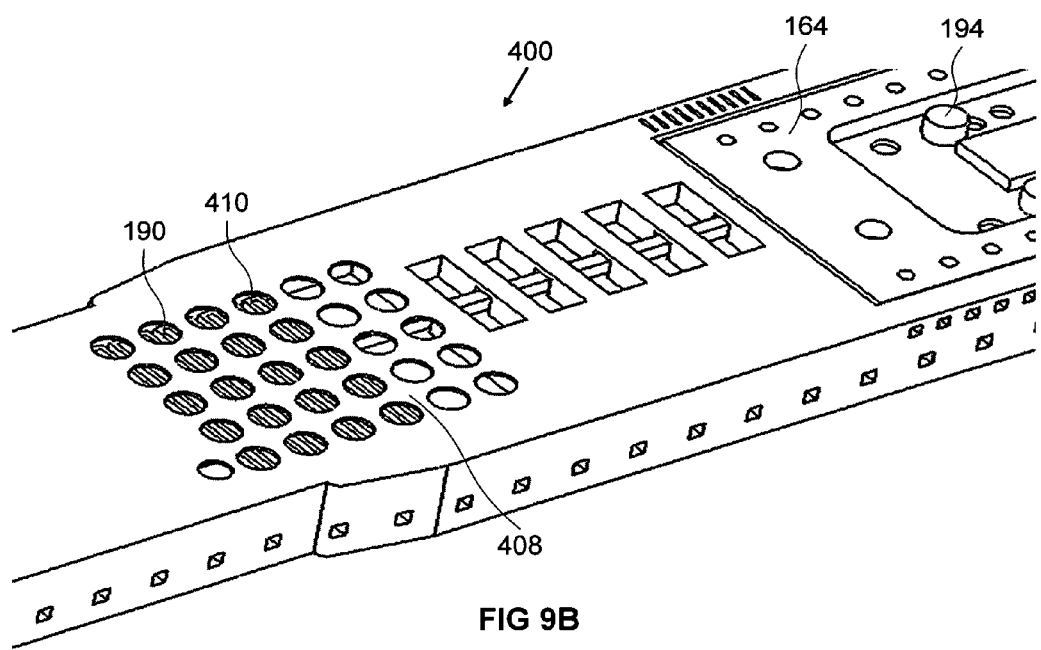
FIG. 9B provides a perspective view of the middle portion of the bottom of the instrument of FIG. 9A FIGS. 10A-10C show various perspective views of a single link of the chain that is used in the instruments of FIGS. 5A or 9A FIG. 10D-10E show two perspective views of two joined links of the chain that is used in the instruments of FIGS. 5A or 9A FIG. 11A provides a perspective view of a sectional view of the distal end of the instrument of FIG. 5A with chain and pulley retention caps removed.

FIG. 9B provides a perspective view of the middle portion of instrument 400 with the pawl spring 190 covered by the bottom of the housing 408 of the instrument with a plurality of release holes 410 located therein to allow easy removal of sacrificial material that may be used during the fabrication of the instrument. Also visible is the distal end of the actuation slide 164 and actuation slide stops 194.

Figure 10A:
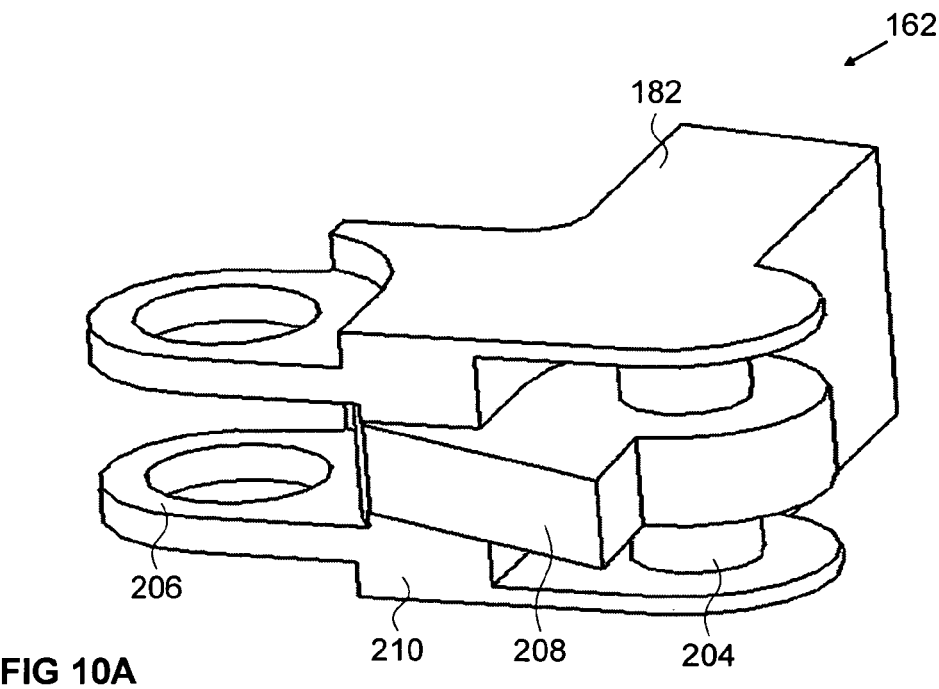
Figure 10B:
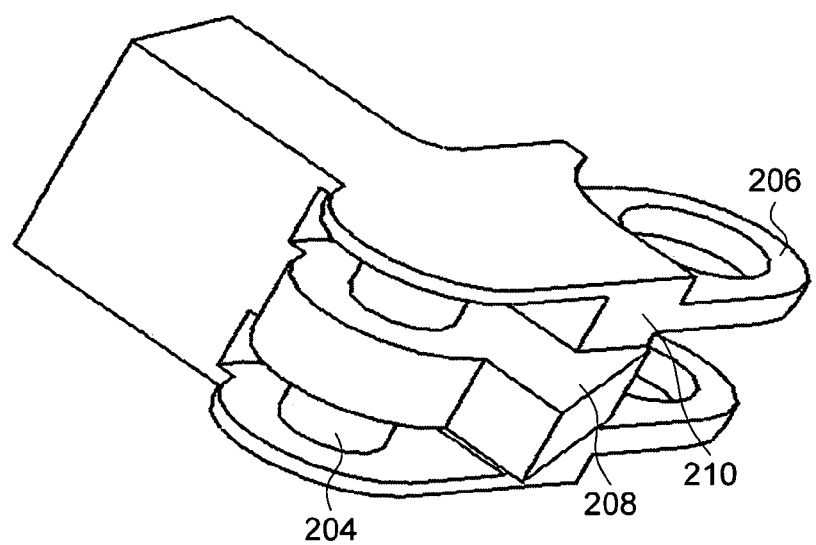
Figure 10C:
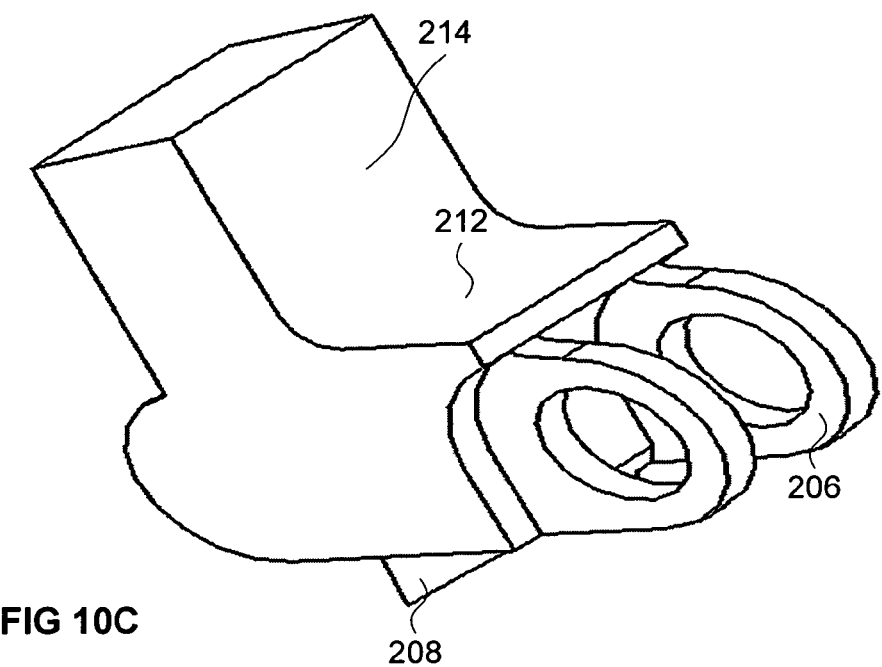
Figure 10D:
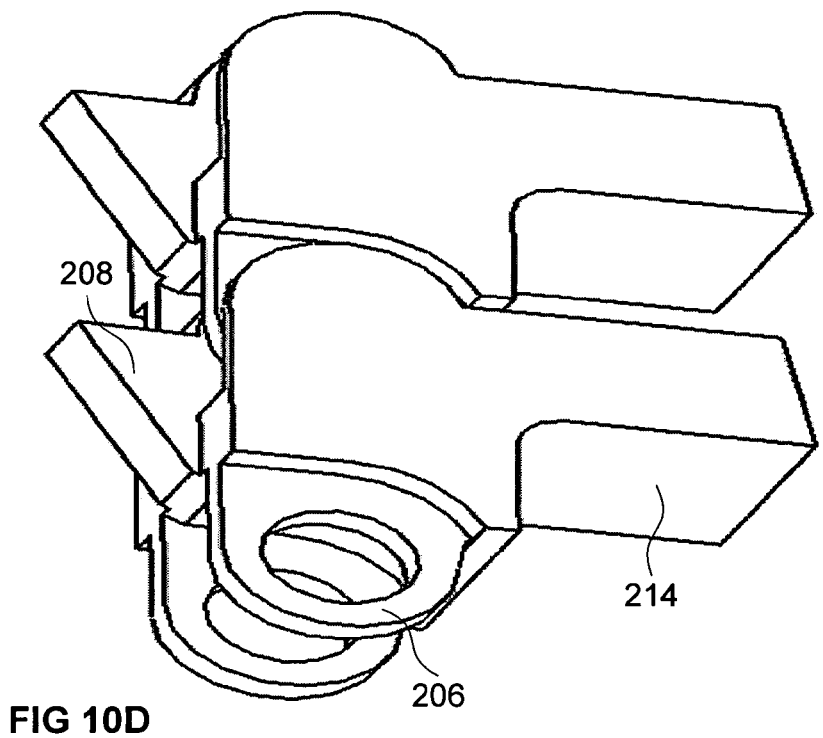
Figure 10E:
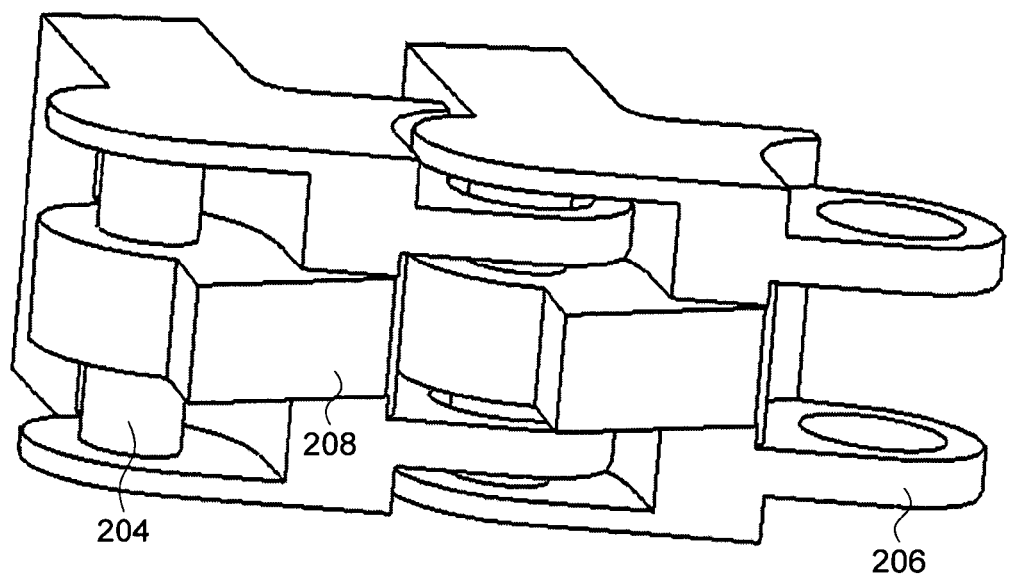

FIGS. 10A-10C show various perspective view of a single link 162 of the chain that is used in either of instrument 100 or instrument 400. In various alternative embodiments, other link configurations are possible. The chain links 162 of this exemplary embodiment include an anvil 182, link pin 204, link ring 206, tooth 208, link base 210, and anvil base 212. Anvil 182 includes a front 214 that, in combination with cutting edge, cuts off tissue and pushes it along the chain path. FIGS. 10D and 10E provide two perspective view of two links that are joined together to form a section of continuous chain. In this exemplary embodiment they are fabricated in the joined position with a small amount of sacrificial material located between the rings and the link pins which keeps the structural materials of the links from adhering together and which can be removed to allow the required joining and relative movement. When joined, the link pin of one link fits into the link ring of the neighboring link. The anvil serves to press tissue against the cutting edges, while the teeth are used to advance the chain. In the configuration of the present exemplary embodiment, a pawl is used to drive the chain over a pulley, instead of a motorized sprocket). The link base 210 makes contact with the rim of the pulleys when the chain is wrapped around them. The anvil base provides a floor to the compartment formed by the anvil and the cutting edges (to be described), as well as stop limiting entry of tissue into the instrument.

Figure 11A:
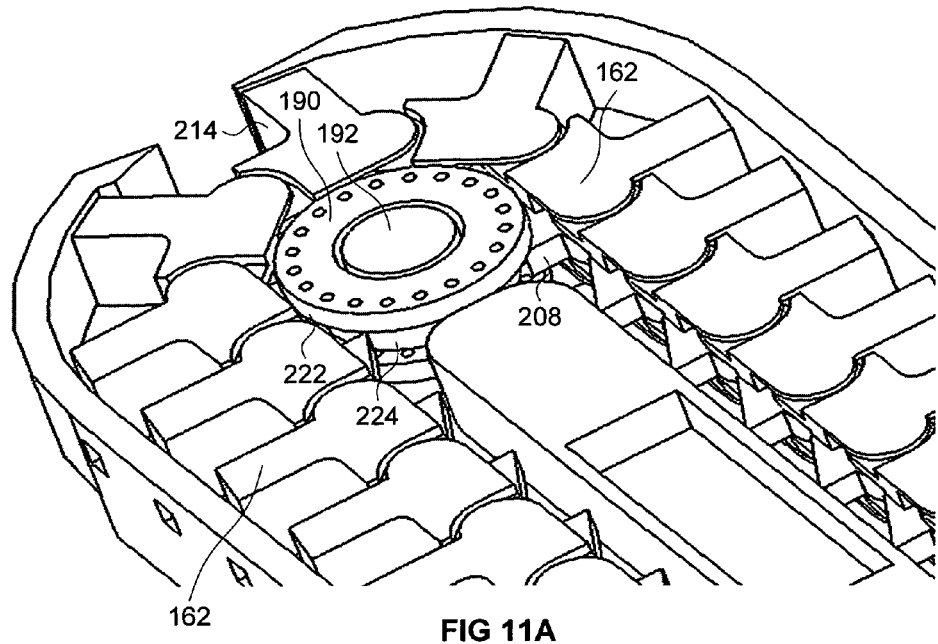
FIG. 11B provides a perspective view of a lower sectional view of the distal end of the instrument of FIG. 5A such that chain link rings and ring links can be seen.
Figure 11B:
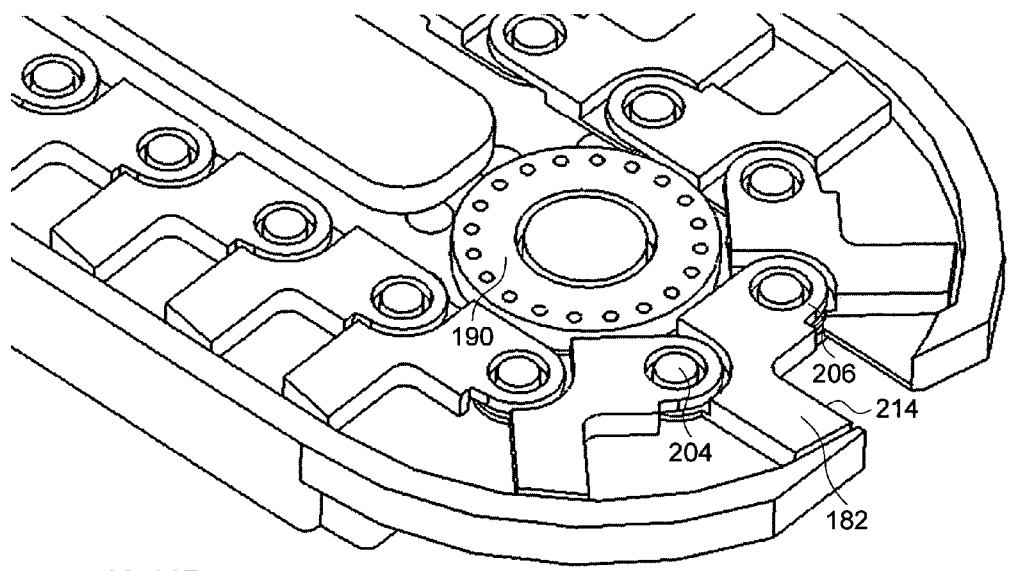
Figure 12A:
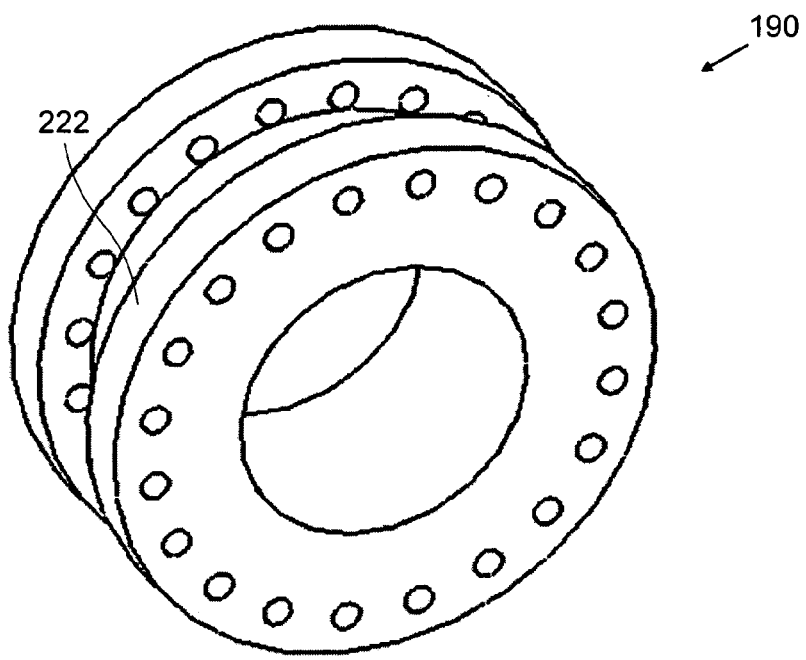
FIGS. 12A and 12B provide perspective views of the pulleys around which the chain of exemplary embodiments of FIGS. 5A and 9A wrap.
Figure 12B:
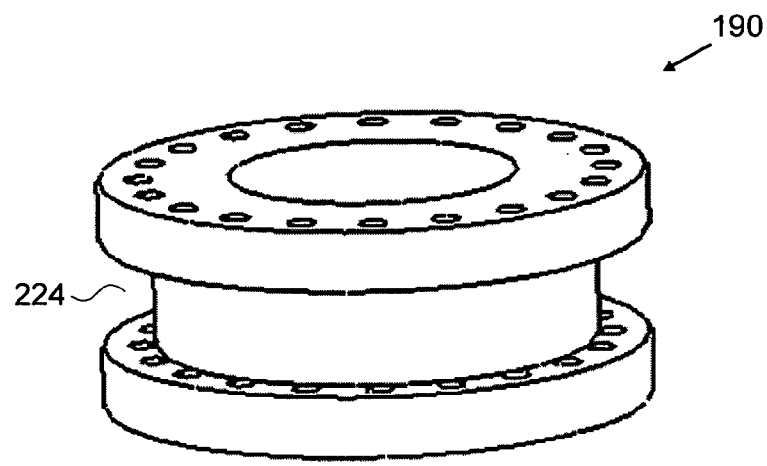
Figure 13:
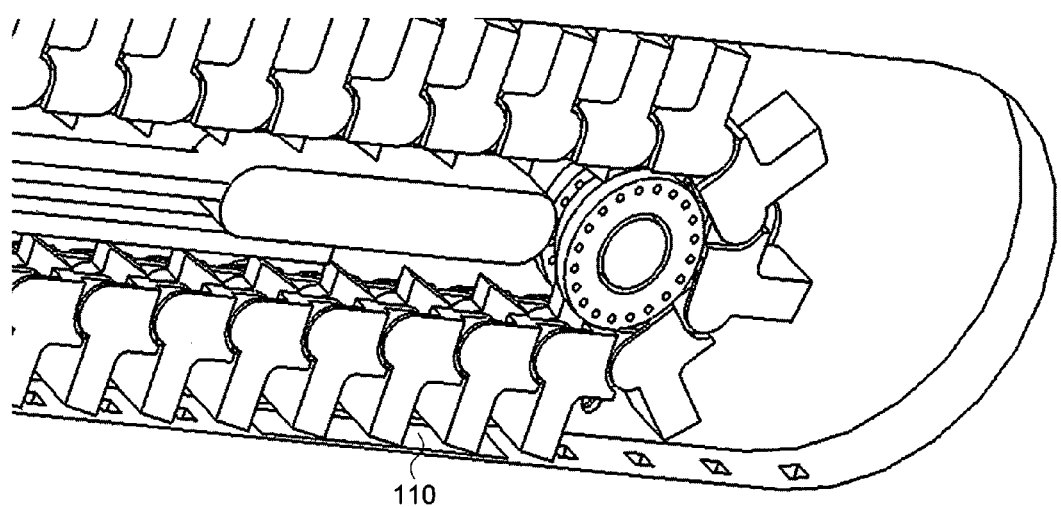
FIG. 13 provides a perspective sectional view (with the caps removed) of the proximal end of the chain along with the proximal pulley.

FIG. 11A provides a perspective view of a sectional view (i.e. caps removed) of distal end of instrument 100 so that the chain links 162, distal pulley 190, and pulley shaft 192 can be seen. of the chain links 162 can be seen. FIGS. 12A and 12B provide perspective views of the pulley 190. As can be seen, the links wrap around the distal pulley 190, with the link bases 210 making contact with the pulley rims 222, while the teeth 208 extend into the tooth relief 224 between the rims. In the present exemplary embodiment, the pulley 190 also includes release holes 230.

FIG. 13A provides a perspective sectional view (with the caps removed) of the proximal end of the chain along with the proximal pulley 190 (which is similar to the distal pulley 190), the cavity 180, and the showing the how the chain wraps around the proximal pulley as it did around the distal pulley.

In the present embodiment, only one specimen inlet is provided in the instrument and it is of approximately the size of the anvil base, so only one link is 'active' (i.e., involved with ablation) at any one time. In alternative embodiments, multiple openings may be provided so that multiple anvils are engaged simultaneously or such that one or more specimen cells may be receiving samples while one or more other cells are cutting samples.

Figure 14A:
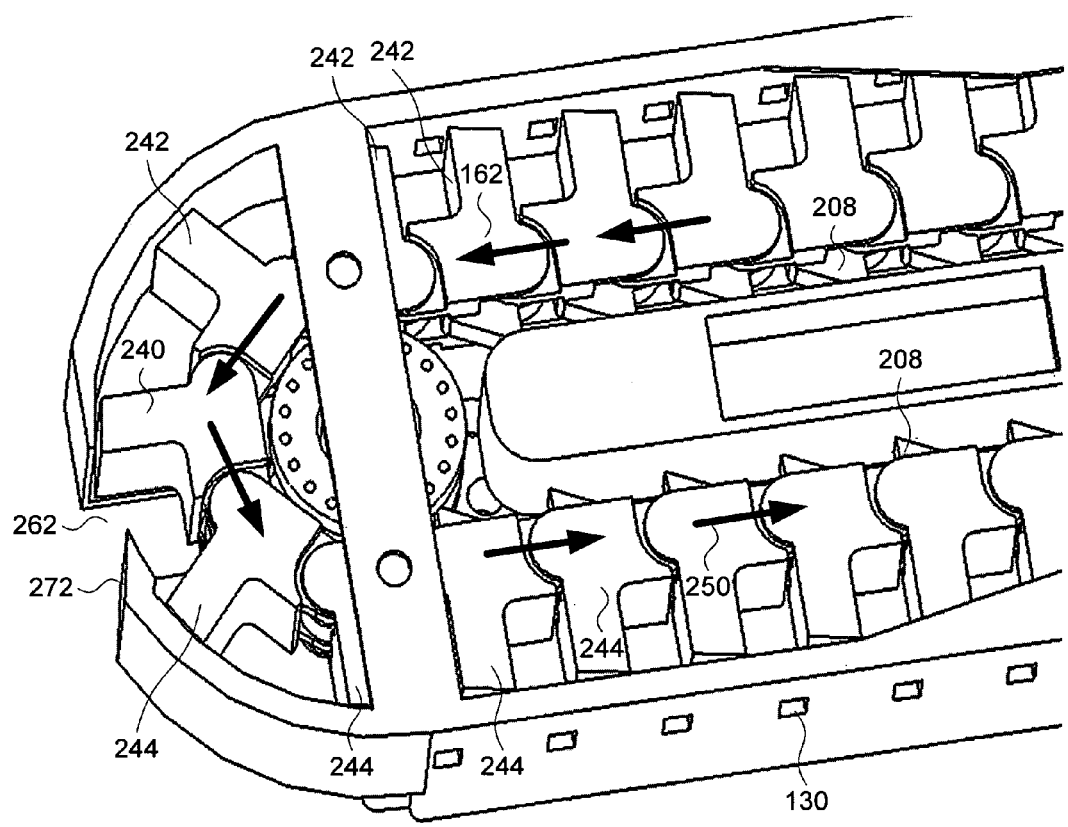
FIG. 14A provides a perspective sectional view of the distal end of the instrument of FIG. 5A with arrows 250 showing the normal direction of travel of the chain.
Figure 14B:
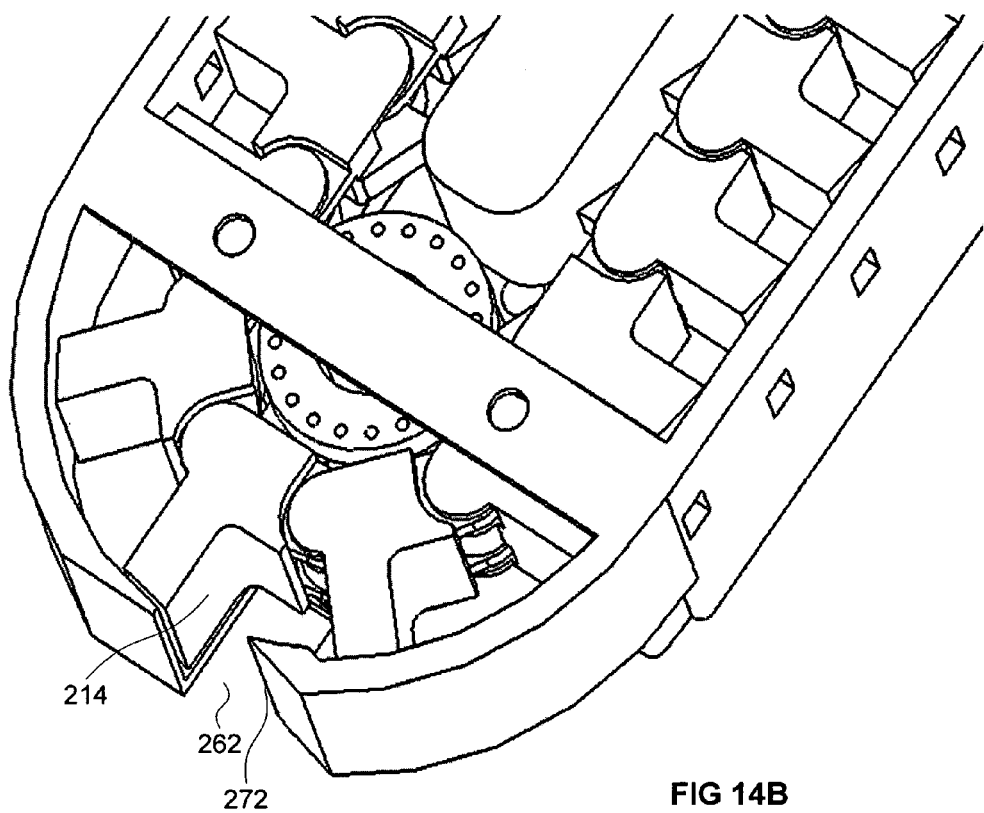
FIG. 14B provides a more magnified view of the distal end of the instrument as compared to that shown in FIG. 14A.

FIG. 14A provides a perspective sectional view of the distal end of the instrument with arrows 250 showing the normal direction of travel of the chain. FIG. 14B provides a more magnified view of the distal end of the instrument as compared to that shown in FIG. 14A. The active link 240 in the region of the inlet 262, pre-active links 242 (i.e., links which have not yet reached the inlet and generally would not be carrying specimens) and post-active links (i.e., links which have already passed the inlet and may be carrying specimens).

Figure 14C:
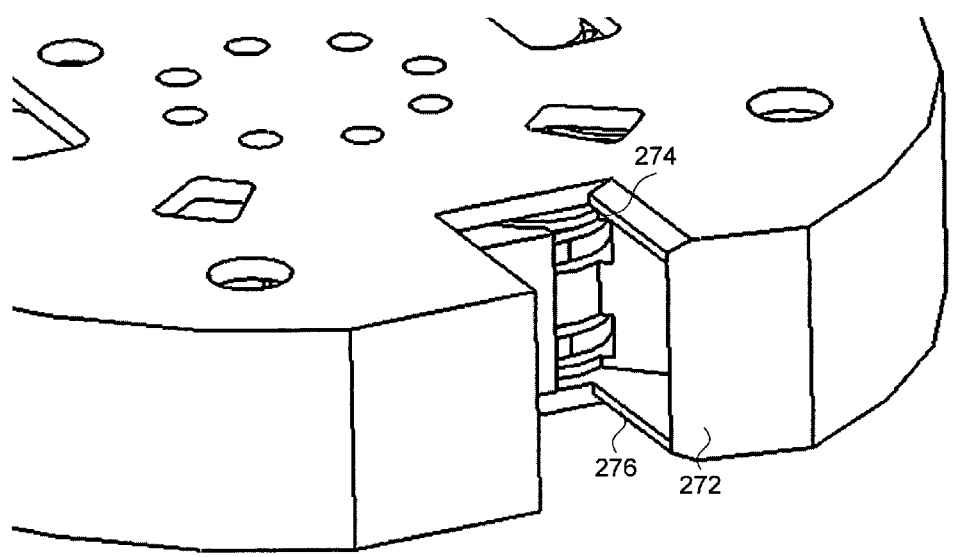
FIG. 14C provides a perspective view of the distal end of instrument 400 where the top of the housing forms the upper horizontal cutting edge FIG. 14D provides a perspective view of lid of the instrument of FIG. 5A with the inlet indention showing chamfered edges to aid in cutting.
Figure 14D:
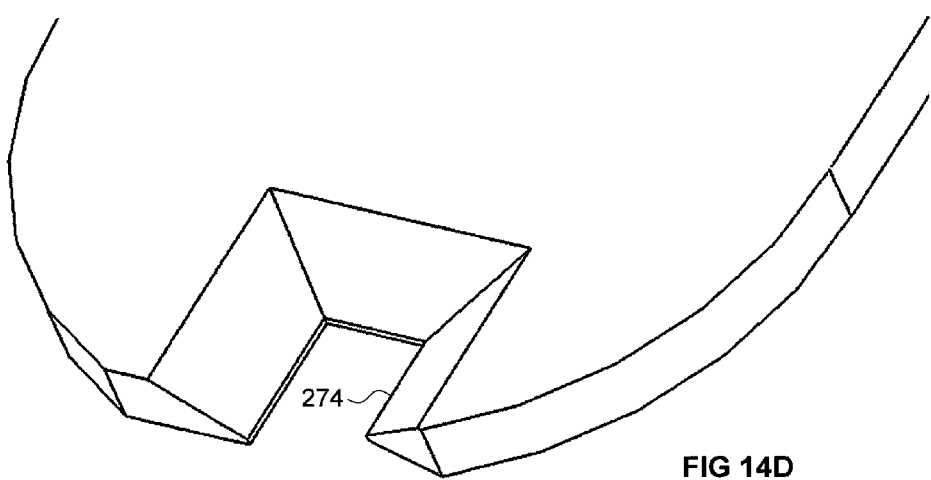

Tissue is introduced to the inlet 262, where the portion extending into the inlet is forced against vertical cutting edge 272 and horizontal cutting edges 274 and 276 (horizontal cutting edges are best seen in the perspective view of the distal end of the lid as shown in FIG. 14D). The cutting edges in effect form a three-sided rectangular tube (preferably with sharp edges) and the anvil in effect serves as a piston moving in this tube, both forcing tissue to be cut away by the edges, and then transported in the direction of the chain motion. FIG. 14C provides a perspective view of the distal end of instrument 400 where the top of the housing forms the upper horizontal cutting edge. FIG. 14D provides a perspective view of lid for instrument 100. The lid 104 is relatively thick to allow handling, in one embodiment the lid features a chamfer around the cutout for the inlet, to allow better tissue access and to provide a sharper upper horizontal cutting edge.

As will be noted from the various figures, the spacing between the anvils is much greater for the links in the region of the inlet than elsewhere, since it is in this region that the links are changing direction by being wrapped around the distal pulley. This effect may be used to advantage: if the tissue parcel that is captured by the instrument is slightly larger than the space between most links, than it will be reliably retained by compression until it is removed by the operator (or reaches the cavity near the proximal pulley where the compression is removed). Of course, if the spacing variation is too large and the tissue is largely incompressible, the chain may be somewhat constrained in moving, so the precise design of pulley radius, link geometry, inlet aperture size, etc. needs to be carefully considered in view of tissue properties.

Figure 15:
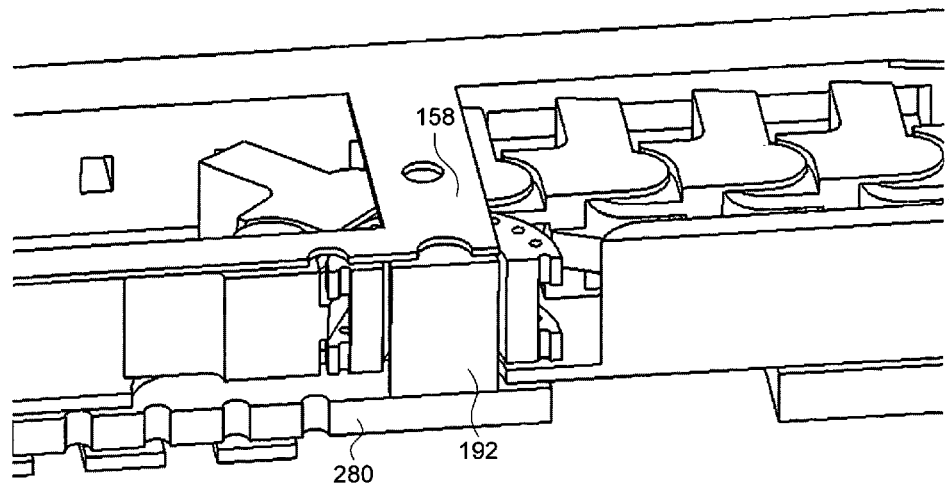
FIG. 15 provides a perspective view of the left half of the instrument of FIG. 5A in the region of the proximal pulley FIG. 16 provides a perspective view of a sliding tensioner for use in the instruments of FIG. 5A or 9A.
Figure 16:
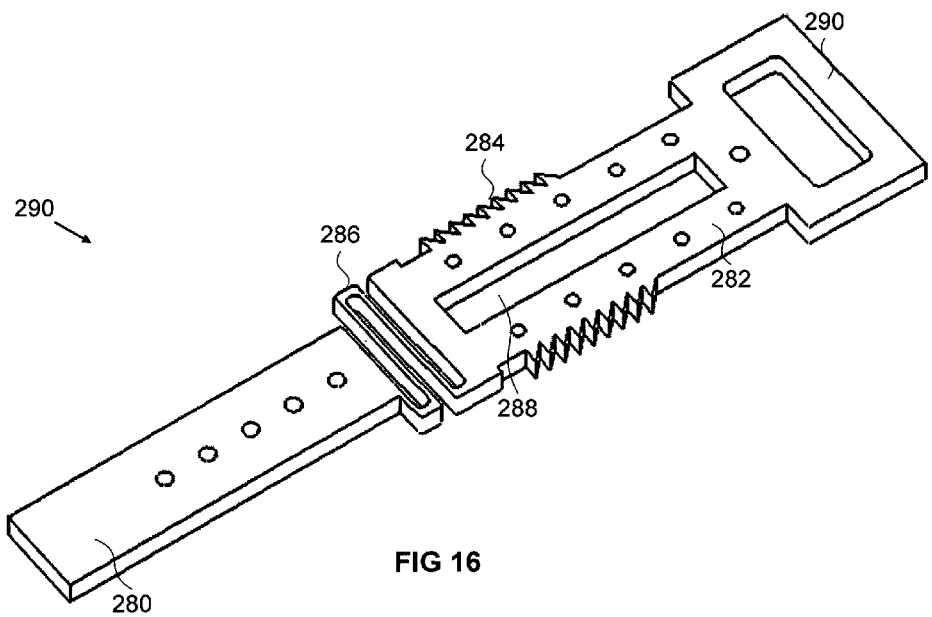
Figure 17A:
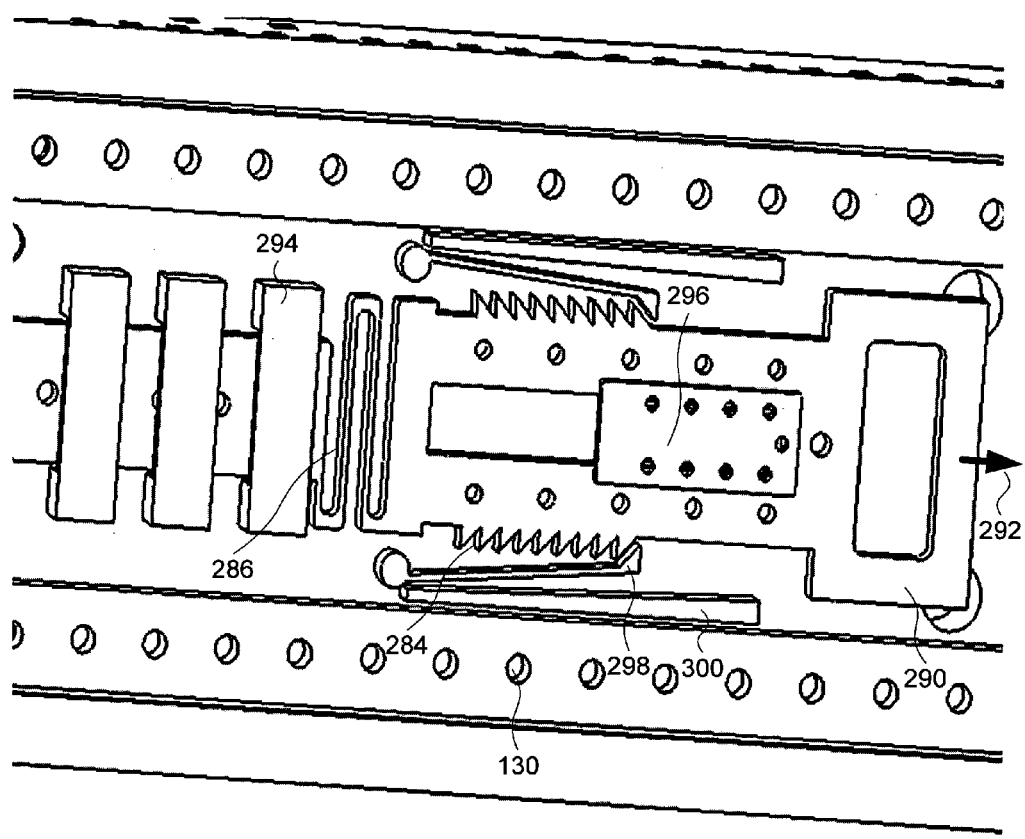
FIGS. 17A and 17B provide a perspective sectional views of a tensioning element and left half of the tensioning element, respectively, for use in the embodiments of FIGS. 5A and 9A.
Figure 17B:
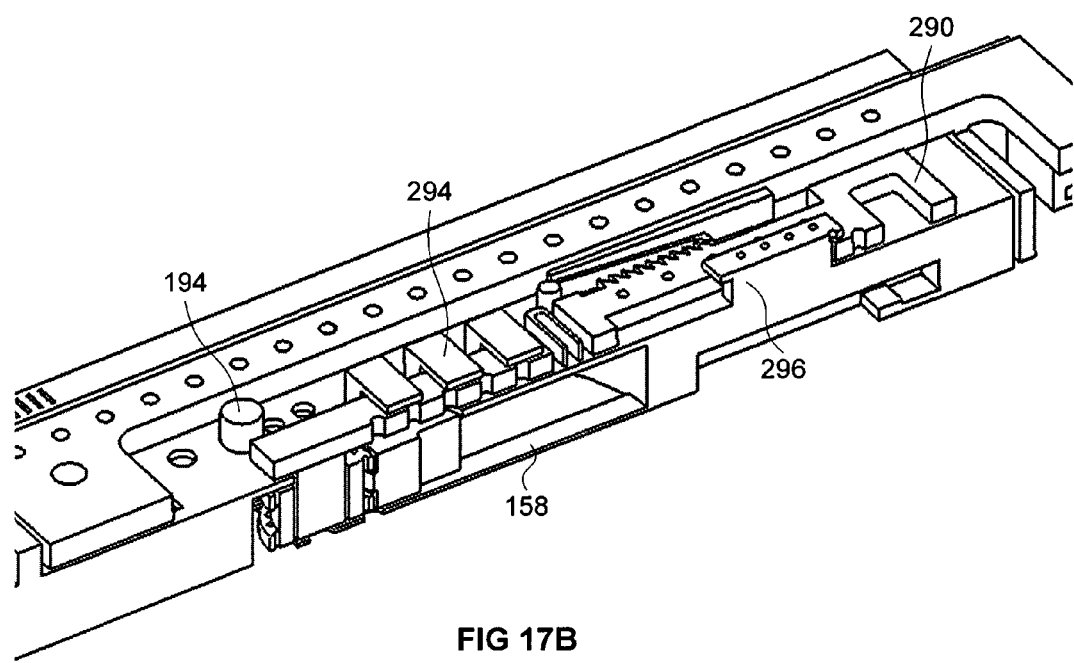

FIG. 15 provides a perspective view of the left half of the instrument 100 in the region of the proximal pulley while FIG. 16 provides a perspective view of a sliding tensioner. The distal pulley is fixed to the housing but the proximal pulley is fixed to the distal tensioner plate 280 of a sliding tensioner 290 that can apply tension to the entire chain and thus remove slack caused by clearance between link rings and link pins, and between the link bases and the pulley rims. As shown in FIG. 16, the tensioner is a sliding device comprising a distal tensioner plate 280 and a proximal tensioner plate 282, separated by a flexure 286. The proximal tensioner plate 282 is provided with tensioning teeth 284 and a tensioning loop 290, the function of which may be understood with the aid of FIGS. 17A and 17B. FIGS. 17A and 17B provide a perspective sectional view of the tensioning element and left half of the tensioning element, respectively. After the instrument is fabricated, force may be applied to the tensioning loop 290 in direction 292 to cause it to slide, guided by the proximal tensioner guides 296 and distal tensioner guides 294. As it slides, the proximal pulley will be pulled along, removing slack from the chain and applying a slight tension to it if desired. When the tensioning loop has been moved sufficiently, the tensioning catches 298 will prevent retrograde motion by lodging within the tensioning teeth. The bumpers 300 prevent excessive outward bowing of the tensioning catches should the force attempting retrograde motion (e.g., the tension in the chain) be excessive. The flexure serves two purposes. First, the ideal amount of travel for the distal tensioner plate may not exactly match the final, resting position of the proximal tensioner plate, as determined by the tensioning teeth and catches, especially since the tensioning teeth are at a fixed, quantized spacing. The compliance of the flexure thus allows the proximal tensioner plate to 'overtravel', moving until the next tooth is engaged by the catch on each side of the plate, without forcing the distal tensioner plate to move by the same amount. A second and related purpose of the flexure, which normally (due to the quantized nature of the teeth) will be flexed, is to provide some compliance to the chain when under tension.

Figure 18A:
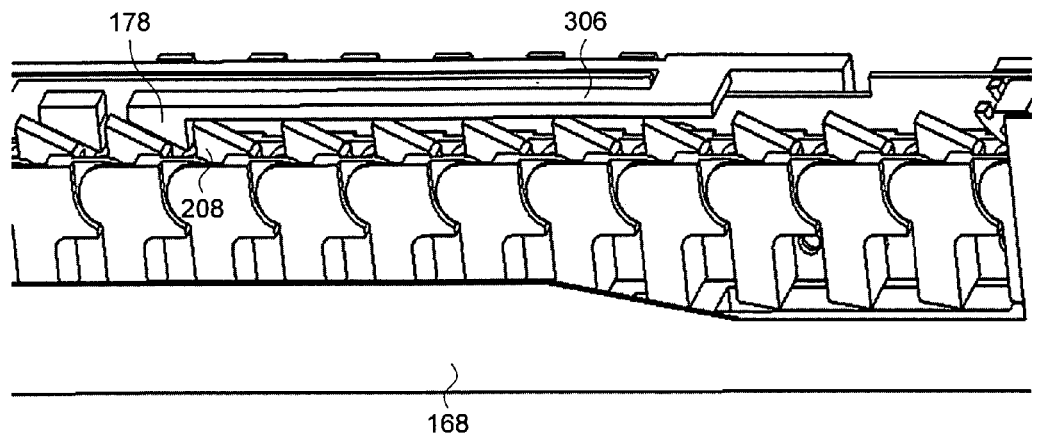
FIGS. 18A and 18B provide sectional perspective views, from the top and bottom, of the left side of the middle portion of the instrument of FIG. 5A such that the relationship between pawl elements and the chain link teeth may be seen.
Figure 18B:
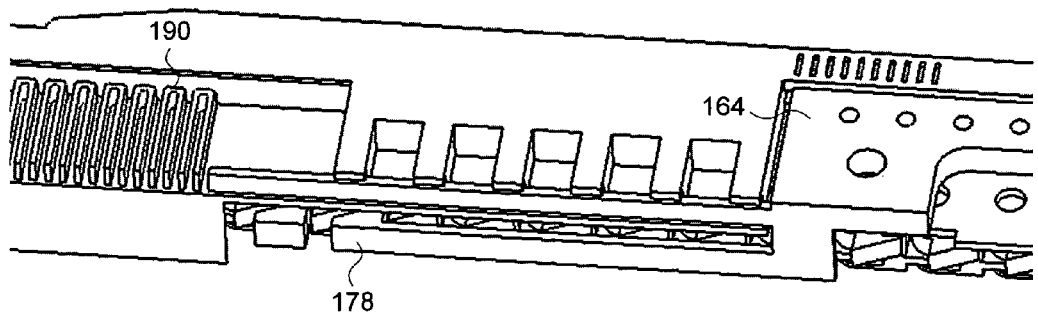

FIGS. 18A and 18B provide sectional perspective views, from the top and bottom, of the left side of the middle portion of the instrument such that the relationship between pawl elements, that extend from the actuation slide 164, and the chain link teeth may be seen. In the exemplary embodiment described herein, the chain is moved by a reciprocating motion of the actuation slide on the lower side of the instrument, which is transmitted to the pawl beam 306 and pawl head 178 as shown in the sectional views of FIGS. 18A and 18B, located within the loop formed by the chain. The pawl head is shaped so as to engage the teeth of the links, forcing the engaged link to move to the right (in the figure) when the pawl head moves in this direction. Meanwhile, when the actuation slide is released, the pawl return spring moves the pawl to the left, forcing the pawl head to ride up over the teeth by virtue of the compliance in the pawl beam, thus returning to a position in which another (typically, the next) link tooth can be engaged. The pawl return spring can be eliminated if the actuation slide is actively returned to its distal position, but is useful if it is desired to only apply tension to the actuation slide, as might be the case, for example, if the instrument is fixed to the end of a long catheter and actuated by a flexible wire or cable.

Figure 19:
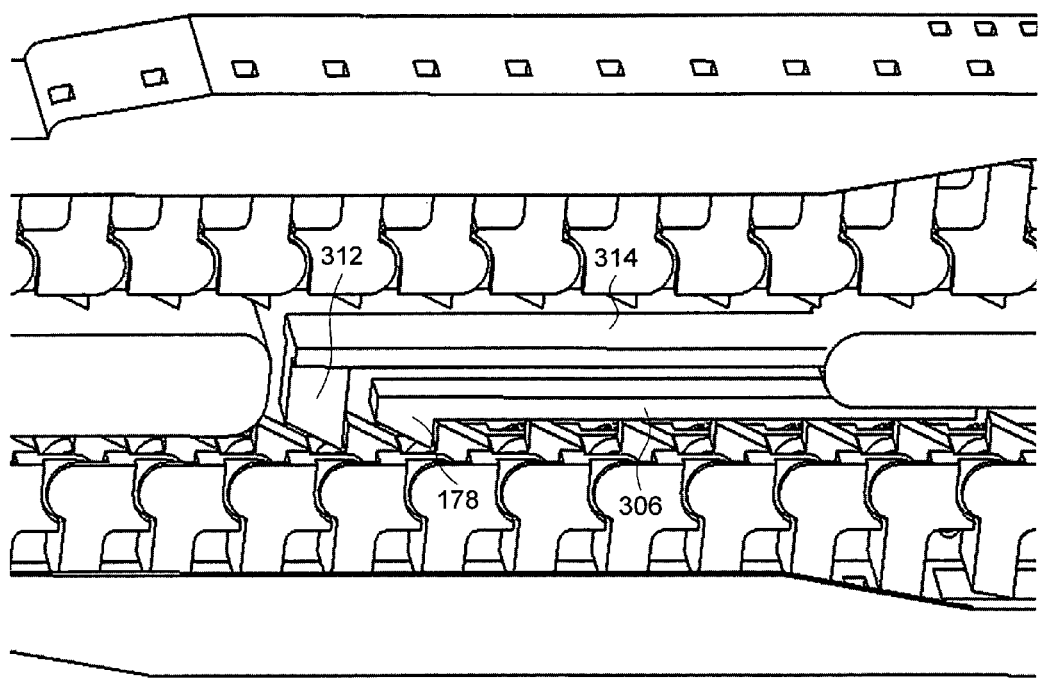
FIG. 19 provides a magnified perspective view of the portion of instrument 100 containing the pawl head and the showing the retaining head and retaining beam which restrains the chain from moving backwards when the pawl head is not engaged.

FIG. 19 provides a magnified perspective view of the portion of instrument 100 containing the pawl head and the showing the retaining head and retaining beam which restrains the chain from moving backwards when the pawl head is not engaged. The translating pawl head 178 and pawl beam 306 are shown along with non-translating retainer head 312 and retainer beam 314. The function of the retainer head is to prevent excessive motion of the chain links to the left (in the figure), especially when the pawl head is not engaged and more particular when it is moving to the left and can tend to drag the chain along with it. Since the retainer head is supported by a compliant beam, it does not prevent rightwards motion of the teeth, since it can ride up over teeth moving in this direction.

Figure 20:
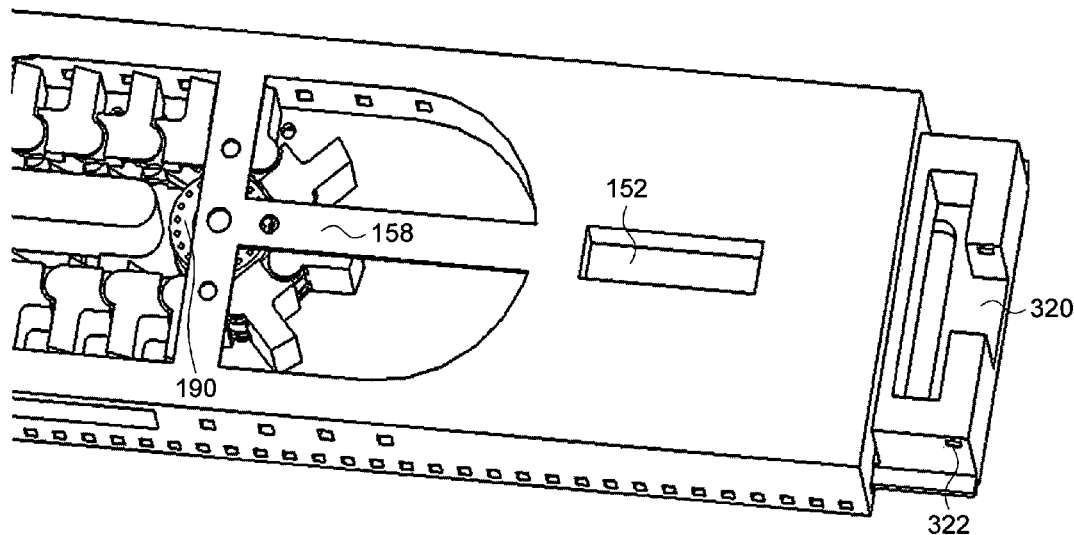
FIG. 20 illustrates the proximal end of the actuation slide which incorporates an interface 320 for the operator.
Figure 21:
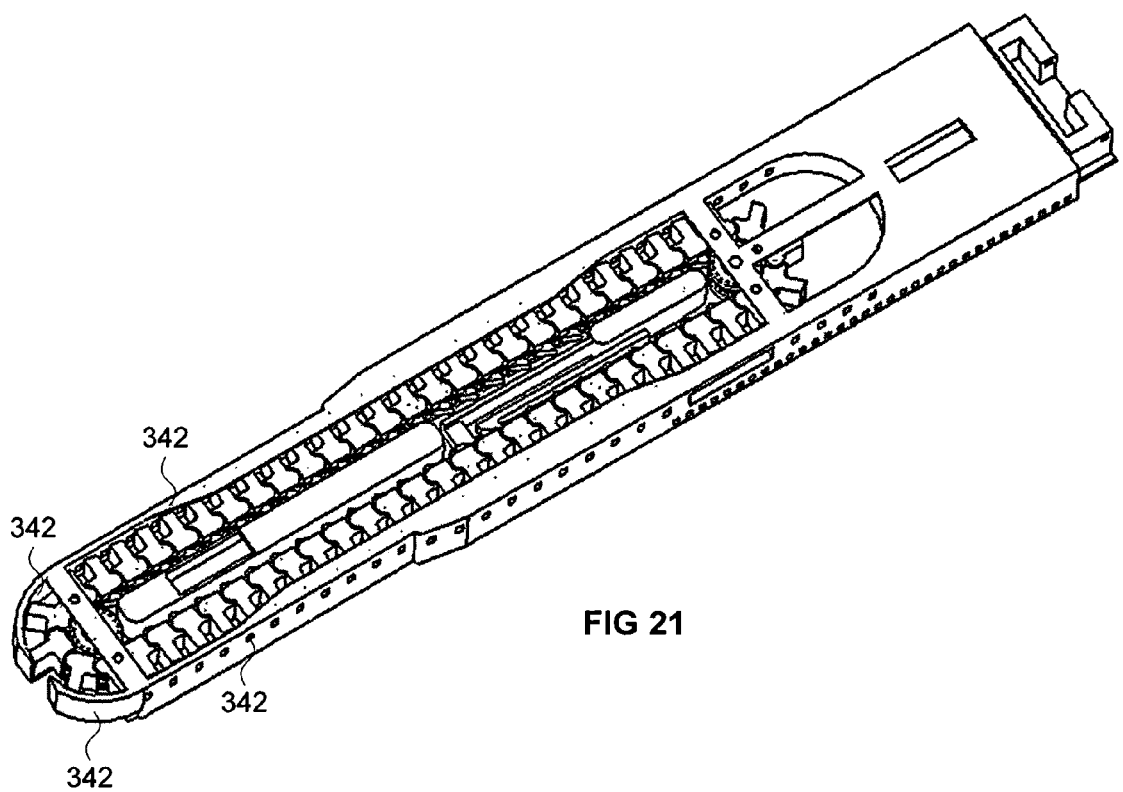
FIG. 21 depicts various alternative locations where inlets may be formed in alternatives of the embodiments of FIGS. 5A and 9A.

FIG. 20 illustrates the proximal end of the actuation slide 164, which incorporates an interface 320 for the operator. A typical interface, as mentioned, would be a wire but other interfaces are possible. In the example, the T-slot shown can accommodate, for example, a T-shaped fitting attached to the end of a wire, or more simply, the end of a wire bent into an L-shape. A small hole 322 is also shown for a wire or pin serving to retain the fitting or wire once inserted into the T-slot. Many other interfaces are of course possible.

Variations of the exemplary embodiments disclosed herein are contemplated. For example, while the instrument shown has its inlet at the extreme distal end, the inlet or additional inlets might located at locations 342 such as those shown in the perspective view of FIG. 21. Moreover, in one embodiment, multiple inlets may be provided, such that multiple links are active simultaneously to ablate tissue from more than one location along the periphery of the instrument at a time. This may allow for a more 'chainsaw' like behavior of the instrument when cutting through larger portions of tissue quickly is required.

While the reciprocating motion of the actuation slide as described above is intended to move the chain by a small amount (i.e., the distance between the fronts of neighboring anvils), longer strokes of the slide (and thus, the pawl head) can cause multiple links to pass the inlet per reciprocating cycle, for faster removal.

It may be desirable to have parcels of tissue accumulate in the cavity (or be issued from the discharge port for the closed version of the instrument, but which can be added to the lid or side of the open version). But it may also be desired, especially for high-speed operation in which the removal rate is large, to flush parcels from the instrument entirely by introducing a flowing liquid (e.g., water or saline), or possibly a gas such as air, into the instrument, e.g., in the area of the cavity. Similarly small amounts of vacuum may be useable to help remove material.

If the curved wall is designed to be fairly close to the anvils (once slack is removed from the chain) such that there is little residual cavity left, then parcels will continue to be transported around the proximal pulley and back in the direction of the distal pulley. If it is desired, for example, to retain parcels in a particular, unscrambled order as described above, then this roughly doubles the number of parcels that can be so retained. Continuing the motion of the parcels even further, the inlet port can serve as a discharge port, particularly once the instrument has been removed from the donor site (and typically, from the patient). Other ports, roughly similar in design to the inlet port but not necessarily with cutting edges, may be designed in any position along the loop of the chain to remove parcels.

The open version of the instrument allows full access to the parcels once the lid is removed. At this time, parcels may be discharged directly from the inter-anvil spaces onto a glass specimen slide, etc. To assist with this discharge, small holes may be provided in the housing of the instrument to allow the insertion of external ejection pins, or ejection mechanisms such as those including retractable pins can be built into the instrument itself.

A version of the instrument is possible in which the anvils are placed on the inside surface of the chain—vs. the outside surface shown in the drawings—if combined with a different pulley design (or group of smaller pulleys). This would enable the inlet port to be located adjacent to the interior surface of the chain. In this configuration, the inlet port may take the form of a hole in the instrument housing, possibly a large hole that allows multiple links to be active simultaneously. The overall effect may be similar to that of an ID saw used on a macroscale in industry (e.g., for slicing wafers from ingots). A possible use of this configuration is cutting reducing the size of structures inserted into the inlet hole.

It should be noted that the teeth are not necessary located on the side of the link opposite the anvil as shown in the figures, and alternative locations are possible.

In an alternative embodiment that uses a different mode of tissue removal, the anvils are replaced by shapes intended to cut or abrade tissue (including bone) without the need for separate, stationery cutting edges. In this embodiment, transport of tissue parcels may not be as easily accomplished, but high-speed removal of tissue with a small instrument may be of compelling value nonetheless.

In some alternative embodiments, depending on the tissue to be removed, it may not be necessary for the cutting edges to be sharpened as the shearing of vertical edges past one another may provide adequate cutting force.

In some alternative embodiments, the drive chain of the present embodiment may be replaced by a flexible or semi-flexible perforated ribbon such that edges of the perforations may be grabbed and anvils pulled along. In other alternative embodiments, instead of providing a chain with multiple anvils, anvils may be provided on a distal pulley or gear elements and chain or ribbon may be provided to engage pulley or gear element to rotate the anvils. In still other alternative embodiments, the pulleys or gear elements may be powered for continuous motion as opposed to reciprocating motion of the exemplary embodiment.

In still other alternative embodiments, the instrument may include a catheter that attaches to or near its proximal end wherein the catheter has an opening along with a cable or other actuation element extends. In still other embodiments, the instrument may include additional elements such as lighting elements, imaging elements, fluid removal elements (e.g. vacuum or blowing elements), cauterizing elements, or the like.

Various other embodiments of the present invention exist. Some of these embodiments may be based on a combination of the teachings herein with various teachings incorporated herein by reference.

As noted above, structural or sacrificial dielectric materials may be incorporated into embodiments of the present invention in a variety of different ways. Such materials may form a third material or higher deposited on selected layers or may form one of the first two materials deposited on some layers. Additional teachings concerning the formation of structures on dielectric substrates and/or the formation of structures that incorporate dielectric materials into the formation process and possibility into the final structures as formed are set forth in a number of patent applications filed Dec. 31, 2003. The first of these filings is U.S. Patent Application No. 60/534,184 which is entitled "Electrochemical Fabrication Methods Incorporating Dielectric Materials and/or Using Dielectric Substrates". The second of these filings is U.S. Patent Application No. 60/533,932, which is entitled "Electrochemical Fabrication Methods Using Dielectric Substrates". The third of these filings is U.S. Patent Application No. 60/534,157, which is entitled "Electrochemical Fabrication Methods Incorporating Dielectric Materials". The fourth of these filings is U.S. Patent Application No. 60/533,891, which is entitled "Methods for Electrochemically Fabricating Structures Incorporating Dielectric Sheets and/or Seed layers That Are Partially Removed Via Planarization". A fifth such filing is U.S. Patent Application No. 60/533,895, which is entitled "Electrochemical Fabrication Method for Producing Multi-layer Three-Dimensional Structures on a Porous Dielectric". Additional patent filings that provide teachings concerning incorporation of dielectrics into the EFAB process include U.S. patent application Ser. No. 11/139,262, filed May 26, 2005 by Lockard, et al., and which is entitled "Methods for Electrochemically Fabricating Structures Using Adhered Masks, Incorporating Dielectric Sheets, and/or Seed Layers that are Partially Removed Via Planarization"; and U.S. patent application Ser. No. 11/029,216, filed Jan. 3, 2005 by Cohen, et al., and which is entitled "Electrochemical Fabrication Methods Incorporating Dielectric Materials and/or Using Dielectric Substrates". These patent filings are each hereby incorporated herein by reference as if set forth in full herein.

The patent applications and patents set forth below are hereby incorporated by reference herein as if set forth in full. The teachings in these incorporated applications can be combined with the teachings of the instant application in many ways: For example, enhanced methods of producing structures may be derived from some combinations of teachings, enhanced structures may be obtainable, enhanced apparatus may be derived, and the like.

| US Pat App No, Filing Date US App Pub No, Pub Date | Inventor, Title |
|---|---|
| 09/493,496 - Jan. 28, 2000 | Cohen, "Method For Electrochemical Fabrication" |
| 10/677,556 - Oct. 1, 2003 | Cohen, "Monolithic Structures Including Alignment and/or Retention Fixtures for Accepting Components" |
| 10/830,262 - Apr. 21, 2004 | Cohen, "Methods of Reducing Interlayer Discontinuities in Electrochemically Fabricated Three-Dimensional Structures" |
| 10/271,574 - Oct. 15, 2002 2003-0127336A - Jul. 10, 2003 | Cohen, "Methods of and Apparatus for Making High Aspect Ratio Micro-electromechanical Structures" |
| 10/697,597 - Dec. 20, 2002 | Lockard, "EFAB Methods and Apparatus Including Spray Metal or Powder Coating Processes" |
| 10/677,498 - Oct. 1, 2003 | Cohen, "Multi-cell Masks and Methods and Apparatus for Using Such Masks To Form Three-Dimensional Structures" |
| 10/724,513 - Nov. 26, 2003 | Cohen, "Non-Conformable Masks and Methods and Apparatus for Forming Three-Dimensional Structures" |
| 10/607,931 - Jun. 27, 2003 | Brown, "Miniature RF and Microwave Components and Methods for Fabricating Such Components" |

-continued

| US Pat App No, Filing Date US App Pub No, Pub Date | Inventor, Title |
|---|---|
| 10/841,100 - May 7, 2004 | Cohen, "Electrochemical Fabrication Methods Including Use of Surface Treatments to Reduce Overplating and/or Planarization During Formation of Multi-layer Three-Dimensional Structures" |
| 10/387,958 - Mar. 13, 2003 2003-022168A - Dec. 4, 2003 | Cohen, "Electrochemical Fabrication Method and Application for Producing Three-Dimensional Structures Having Improved Surface Finish" |
| 10/434,494 - May 7, 2003 2004-0000489A - Jan. 1, 2004 | Zhang, "Methods and Apparatus for Monitoring Deposition Quality During Conformable Contact Mask Plating Operations" |
| 10/434,289 - May 7, 2003 20040065555A - Apr. 8, 2004 | Zhang, "Conformable Contact Masking Methods and Apparatus Utilizing In Situ Cathodic Activation of a Substrate" |
| 10/434,294 - May 7, 2003 2004-0065550A - Apr. 8, 2004 | Zhang, "Electrochemical Fabrication Methods With Enhanced Post Deposition Processing Enhanced Post Deposition Processing" |
| 10/434,295 - May 7, 2003 2004-0004001A - Jan. 8, 2004 | Cohen, "Method of and Apparatus for Forming Three-Dimensional Structures Integral With Semiconductor Based Circuitry" |
| 10/434,315 - May 7, 2003 2003-0234179 A - Dec. 25, 2003 | Bang, "Methods of and Apparatus for Molding Structures Using Sacrificial Metal Patterns" |
| 10/434,103 - May 7, 2004 2004-0020782A - Feb. 5, 2004 | Cohen, "Electrochemically Fabricated Hermetically Sealed Microstructures and Methods of and Apparatus for Producing Such Structures" |
| 10/841,006 - May 7, 2004 | Thompson, "Electrochemically Fabricated Structures Having Dielectric or Active Bases and Methods of and Apparatus for Producing Such Structures" |
| 10/434,519 - May 7, 2003 2004-0007470A - Jan. 15, 2004 | Smalley, "Methods of and Apparatus for Electrochemically Fabricating Structures Via Interlaced Layers or Via Selective Etching and Filling of Voids" |
| 10/724,515 - Nov. 26, 2003 | Cohen, "Method for Electrochemically Forming Structures Including Non- Parallel Mating of Contact Masks and Substrates" |
| 10/841,347 - May 7, 2004 | Cohen, "Multi-step Release Method for Electrochemically Fabricated Structures" |
| 60/533,947 - Dec. 31, 2003 | Kumar, "Probe Arrays and Method for Making" |
| 60/534,183 - Dec. 31, 2003 | Cohen, "Method and Apparatus for Maintaining Parallelism of Layers and/or Achieving Desired Thicknesses of Layers During the Electrochemical Fabrication of Structures" |

If a conflict exists between definitions or terminology supplied directly herein and definition or terminology supplied in one or more of the applications, patents, or publications incorporated herein by reference, the definitions of terms supplied directly herein shall be considered the definitions intended for use by the Applicant.

It is not intended that the headers be used to limit the application of teachings found in one portion of the specification from applying to other portions of the specification. For example, it should be understood that alternatives acknowledged in association with one embodiment, are intended to apply to all embodiments to the extent that the features of the different embodiments make such application functional and do not otherwise contradict or remove all benefits of the adopted embodiment. Various other embodiments of the present invention exist. Some of these embodiments may be based on a combination of the teachings herein with various teachings incorporated herein by reference.

In view of the teachings herein, many further embodiments, alternatives in design and uses of the embodiments of the instant invention will be apparent to those of skill in the art. As such, it is not intended that the invention be limited to the particular illustrative embodiments, alternatives, and uses described above but instead that it be solely limited by the claims presented hereafter.

I claim:

1. A medical instrument for removing specimens of tissue from a patient's body during a minimally invasive surgical procedure, comprising:
    (a) an elongated housing having a distal end and a proximal end;
    (b) an inlet to the housing located near the distal end of the housing;
    (c) two rotary elements supported directly or indirectly by the housing, one of which is located near the distal end of the housing and the other of which is located closer to the proximal end of the housing;
    (d) an elongated member selected from the group comprising a flexible member and a bendable member, wherein the elongated member extends around the rotary elements and wherein the elongated member may be made to move in a desired direction by an activation mechanism; and
    (e) a plurality of anvils located on the elongated, such that when the elongated member is moved, the anvils, in turn, rotate past the at least one opening, and such that when tissue is located in the inlet at least a portion of the tissue is removed by the interaction of the anvil with an edge of the housing, wherein the removed tissue is transported within the housing away from the inlet toward the proximal end of the housing.

2. The medical instrument of claim 1 further comprising a catheter that is attached to or near the distal end of the device wherein the catheter includes a passage for passing an actuation control element.

3. The medical instrument of claim 1 wherein the rotary elements comprise a pulley.

4. The medical instrument of claim 1 wherein the rotary elements comprise a gear.

5. The medical instrument of claim 1 wherein the elongated member comprises a chain.

6. The medical instrument of claim 1 wherein the elongated member comprises a perforated ribbon.

7. The medical instrument of claim 1 additionally comprising a tensioning mechanism that is capable of increasing a distance between the rotary elements.

8. The medical instrument of claim 1 additionally comprising a pawl mechanism and a compliant return member for moving the elongated member around the rotary elements in a desired direction.

9. The medical instrument of claim 8 additionally comprising a retention element for holding the elongated member in a fixed position while the pawl head is moving from a proximally engaged location through an unengaged region to a more distally engaged location along the elongated member.

10. The medical instrument of claim 1 wherein the instrument is formed from a plurality of successively deposited layers of material where each layer comprises at least one sacrificial material and at least one structural material and wherein each successive layer is adhered to a previously formed layer as the successive layer is being formed.

11. A medical instrument for removing specimens of tissue from a patient's body during a minimally invasive surgical procedure, comprising:
    (a) an elongated housing having a distal end and a proximal end;
    (b) an inlet to the housing located near the distal end of the housing;
    (c) two rotary elements supported directly or indirectly by the housing, one of which is located near the distal end of the housing and the other of which is located closer to the proximal end of the housing;
    (d) an elongated member selected from the group comprising a flexible member and a bendable member, wherein the elongated member extends around the rotary elements and wherein the elongated member may be made to move in a desired direction by an activation mechanism; and
    (e) a plurality of anvils located on the distally located rotary element, such that when the elongated flexible or bendable element is moved, the anvils, in turn, rotate past the at least one opening, and such that when tissue is located in the inlet at least a portion of the tissue is removed by the interaction of the anvil with an edge of the housing, wherein the removed tissue is transported within the housing away from the inlet toward the proximal end of the housing.

12. The medical instrument of claim 11 further comprising a catheter that is attached to or near the distal end of the device wherein the catheter includes a passage for passing an actuation control element.

13. The medical instrument of claim 11 wherein the rotary elements comprise a gear.

14. The medical instrument of claim 1 wherein the elongated member comprises a chain.

15. The medical instrument of claim 11 additionally comprising a tensioning mechanism that is capable of increasing a distance between the rotary elements.

16. The medical instrument of claim 11 additionally comprising a pawl mechanism and a compliant return member for moving the elongated member around the rotary elements in a desired direction.

17. The medical instrument of claim 16 additionally comprising a retention element for holding the elongated member in a fixed position while the pawl head is moving from a proximally engaged location through an unengaged region to a more distally engaged location along the elongated member.

* * * * *